US012661441B2

(12) United States Patent

Manda

(10) Patent No.: US 12,661,441 B2
(45) Date of Patent: Jun. 23, 2026

(54) DIALYSIS CATHETER INCLUDING PRESSURE AND IMPEDANCE SENSORS

(71) Applicant: MOZARC MEDICAL US LLC, Minneapolis, MN (US)

(72) Inventor: Venkatesh Manda, Stillwater, MN (US)

(73) Assignee: MOZARC MEDICAL US LLC, Minneapolis, MN (US)

( * ) Notice: Subject to any disclaimer, the term of this patent is extended or adjusted under 35 U.S.C. 154(b) by 439 days.

(21) Appl. No.: 17/397,358

(22) Filed: Aug. 9, 2021

(65) Prior Publication Data

US 2022/0047793 A1     Feb. 17, 2022

Related U.S. Application Data

(60) Provisional application No. 63/064,681, filed on Aug. 12, 2020.

(51) Int. Cl.
*A61M 1/28* (2006.01)
(52) U.S. Cl.
CPC ............ *A61M 1/285* (2013.01); *A61M 1/282* (2014.02); *A61M 2205/3331* (2013.01); *A61M 2205/3553* (2013.01); *A61M 2205/502* (2013.01)

(58) Field of Classification Search
CPC .. A61M 2205/3331; A61M 2205/3344; A61M 2205/3351; A61M 2205/3355; A61M 5/3334; A61M 1/285; A61M 1/282; A61M 1/281; A61M 1/155; A61M 25/0029; A61M 25/0028; A61M 1/28; A61M 1/159; A61M 2210/1017; A61M 1/14;

(Continued)

(56) References Cited

U.S. PATENT DOCUMENTS 5,376,244 A     12/1994  Preidel
5,433,216 A      7/1995  Sugrue et al.
(Continued)

FOREIGN PATENT DOCUMENTS

CN        102599892 A     7/2012
WO      2006054720 A1     5/2006

OTHER PUBLICATIONS

"Mikro-Cath Pressure Catheter," "All pressure catheters are not created equal", Millar, Received on Feb. 21, 2020, retrieved from https://millar.com/content/documents/Knowledge_Center/Cutsheets_and_Brochures/Mikro_Cath_005_1070_C.pdf, 2 pp.

*Primary Examiner* — Michael J Tsai
*Assistant Examiner* — Kathleen Paige Farrell

(57)     ABSTRACT

In examples described herein, a catheter configured to deliver dialysate and extract an effluent fluid from a peritoneal cavity of a patient includes at least two sensors configured and positioned to generate respective signals indicative of one or more parameters related to PD treatment provided to the patient. The sensors can include, for example, a pressure sensor configured to generate a pressure signal indicative of a pressure of a fluid within a lumen of the catheter or external to the catheter and an impedance sensor configured to generate an impedance signal indicative of an impedance of a fluid within the lumen of the catheter or external to the catheter. A parameter related to PD treatment can include, for example, a catheter status or a peritoneal cavity status of the patient.

37 Claims, 9 Drawing Sheets

(58) Field of Classification Search

CPC ............ A61M 1/16; A61M 2205/3334; A61M 1/1565; A61M 2205/52; A61M 1/3656; A61M 2205/3379; A61M 1/34; A61M 2205/3317; A61M 2230/65; A61M 1/3669; A61M 2205/50; A61M 1/284; A61M 1/287; A61M 1/32; A61M 1/3653; A61M 1/3661; A61M 1/154; A61M 2205/3327; A61B 5/0295; A61B 5/0537; A61B 5/053; A61B 5/6866; A61B 5/0215; A61B 5/0538; A61B 5/14503; A61B 2562/0247

See application file for complete search history.

(56) References Cited

U.S. PATENT DOCUMENTS

| | | | |
|---|---|---|---|
| 5,476,447 A | 12/1995 | Noda et al. | |
| 5,951,539 A | 9/1999 | Nita et al. | |
| 6,228,047 B1 | 5/2001 | Dadson | |
| 6,394,986 B1 | 5/2002 | Millar | |
| 6,398,738 B1 | 6/2002 | Millar | |
| 6,409,699 B1 | 6/2002 | Ash | |
| 6,817,983 B1 | 11/2004 | Millar | |
| 7,013,702 B1 | 3/2006 | Millar | |
| 7,507,220 B2 | 3/2009 | Childers et al. | |
| 8,206,339 B2 | 6/2012 | Childers et al. | |
| 8,323,231 B2 | 12/2012 | Childers et al. | |
| 8,992,461 B2 | 3/2015 | Tedmann et al. | |
| 9,039,652 B2 | 5/2015 | Degen et al. | |
| 9,095,655 B2 | 8/2015 | Hedmann et al. | |
| 9,333,365 B2 | 5/2016 | Zhao | |
| 9,907,897 B2 | 3/2018 | Burbank et al. | |
| 10,646,122 B2 * | 5/2020 | McCaffrey et al. | A61B 5/6852 |
| 2005/0115561 A1 * | 6/2005 | Stahmann | A61N 1/3601 |
| | | | 128/204.23 |
| 2007/0088323 A1 * | 4/2007 | Campbell | A61M 25/10 |
| | | | 604/523 |
| 2008/0027332 A1 | 1/2008 | Bradley | |
| 2008/0294041 A1 * | 11/2008 | Kassab | A61B 5/02007 |
| | | | 600/433 |
| 2010/0004590 A1 | 1/2010 | Hedmann et al. | |
| 2010/0121159 A1 | 5/2010 | Burnett et al. | |
| 2012/0277655 A1 * | 11/2012 | Gerber | A61B 5/053 |
| | | | 604/503 |
| 2014/0018727 A1 | 1/2014 | Burbank et al. | |
| 2014/0135878 A1 | 5/2014 | Burnett et al. | |
| 2014/0326671 A1 * | 11/2014 | Kelly | B01J 20/20 |
| | | | 210/287 |
| 2015/0157216 A1 * | 6/2015 | Stigall et al. | A61M 25/0045 |
| 2016/0331926 A1 | 11/2016 | Bueche et al. | |
| 2018/0043078 A1 | 2/2018 | Gerber et al. | |
| 2018/0311071 A1 * | 11/2018 | Burnett | A61F 7/0085 |
| 2019/0247680 A1 * | 8/2019 | Mayer et al. | G16H 20/40 |
| 2019/0321535 A1 * | 10/2019 | Beavers | A61M 1/71 |
| 2020/0030517 A1 * | 1/2020 | Basati | A61M 1/159 |
| 2020/0046230 A1 * | 2/2020 | McCaffrey | A61B 5/6851 |
| 2021/0346675 A1 | 11/2021 | Schlebusch | |

* cited by examiner

100

110

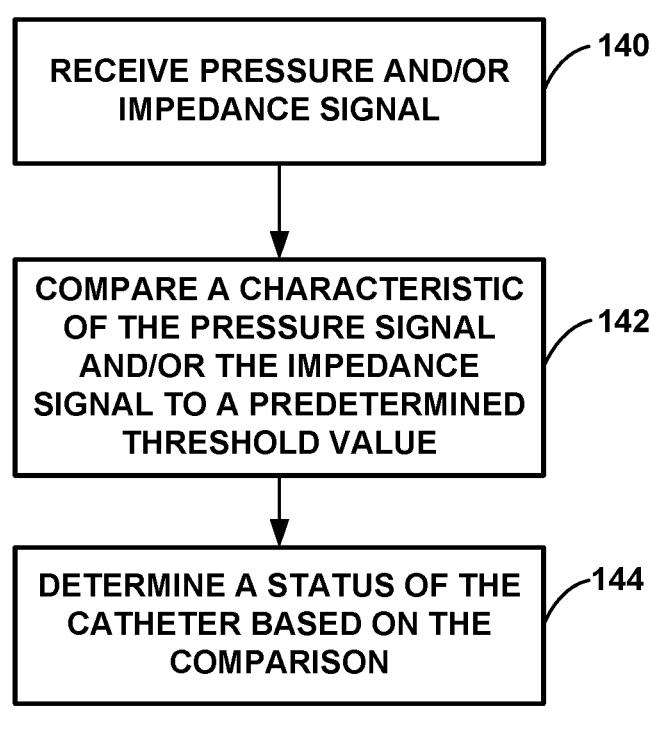

RECEIVE PRESSURE AND/OR IMPEDANCE SIGNAL ⌐140

COMPARE A CHARACTERISTIC OF THE PRESSURE SIGNAL AND/OR THE IMPEDANCE SIGNAL TO A PREDETERMINED THRESHOLD VALUE ⌐142

DETERMINE A STATUS OF THE CATHETER BASED ON THE COMPARISON ⌐144

FIG. 13

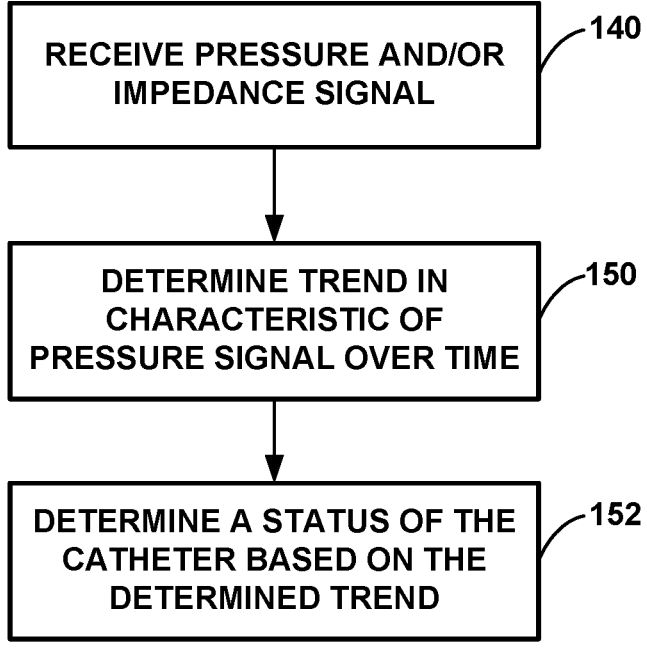

RECEIVE PRESSURE AND/OR IMPEDANCE SIGNAL ⌐140

DETERMINE TREND IN CHARACTERISTIC OF PRESSURE SIGNAL OVER TIME ⌐150

DETERMINE A STATUS OF THE CATHETER BASED ON THE DETERMINED TREND ⌐152

FIG. 14

RECEIVE PRESSURE AND/OR IMPEDANCE SIGNAL ⌐156

COMPARE CHARACTERISTIC OF RECEIVED SIGNAL(S) TO A PREDETERMINED THRESHOLD VALUE OR DETERMINE TREND IN THE CHARACTERISTIC OVER TIME ⌐158

CONTROL OPERATION OF PD SYSTEM BASED ON THE COMPARISON AND/OR THE DETERMINED TREND ⌐160

DIALYSIS CATHETER INCLUDING PRESSURE AND IMPEDANCE SENSORS

This application claims the benefit of U.S. Provisional Application No. 63/064,681, filed Aug. 12, 2020, and entitled, "DIALYSIS CATHETER INCLUDING PRESSURE AND IMPEDANCE SENSORS," the entire content of which is incorporated herein by reference.

TECHNICAL FIELD

The present disclosure relates to dialysis catheters.

BACKGROUND

Peritoneal dialysis (PD) may be used to remove waste products from blood of a patient when the kidneys of the patient are no longer able to adequately do so. During PD, a PD cycler delivers a dialysate through a catheter into a peritoneal cavity of a patient. The peritoneum of the patient acts as a membrane through which waste products are removed from the blood of the patient via osmosis and diffusion. Waste products and fluid pass from the blood of the patient, through the peritoneum, and into the dialysate. After a dwell period, the PD cycler removes an effluent fluid from the peritoneal cavity, which includes the dialysate and filtered waste products, from the patient's peritoneal cavity through the catheter.

SUMMARY

This disclosure describes example devices, systems, and techniques for monitoring a PD system and related patient parameters. In examples described herein, a catheter configured to deliver dialysate and extract an effluent fluid from a peritoneal cavity of a patient includes a plurality of sensors configured and positioned to generate respective signals indicative of one or more parameters related to PD treatment provided to the patient. The sensors can include, for example, a pressure sensor configured to generate a pressure signal indicative of a pressure of a fluid within a lumen of the catheter or external to the catheter and an impedance sensor configured to generate an impedance signal indicative of an impedance of the system in response to a fluid within the lumen of the catheter or external to the catheter. Sensors placed internal or external to the peritoneal cavity have unique and different advantages. A parameter related to PD treatment can include, for example, a catheter patency status or a peritoneal hemodynamic status, respectively. The catheter patency status (also referred to herein generally as a catheter status) can be indicative of a catheter obstruction that has occurred due to, for example, one or more of tissue in-growth around an opening of the catheter, a blockage within a lumen of the catheter, or a kink in the catheter. A peritoneal hemodynamic status can indicate, for example, a hemodynamic status (or change) in the patient, such as an indication of whether a particular amount of fluid (e.g., considered to be abnormal) is present within the peritoneal cavity, a physiologic or non-physiologic pressure change in the peritoneal cavity, relative changes in the amount of fluid and/or pressure in the peritoneal cavity, or any combinations thereof.

Detection of the one or more parameters related to PD treatment using one or more of the sensors described herein may enable a patient and/or a clinician to monitor PD treatment (e.g., adequacy of or need to titrate a given PD prescription) and intervene to provide adjustments to the PD prescription (e.g., dwell period, a concentration of osmotic agents in the dialysate delivered to the patient, or the like) or address any issues (e.g., catheter obstruction) that may adversely impact the efficacy of the PD treatment. A clinician may be able to evaluate, observe trends, determine an efficacy of the PD treatment, and/or adjust one or more parameters of the PD treatment, based on the information from the one or more sensors, in order to fit particular patient needs or mitigate issues associated with the PD treatment system.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIGS. 13-15 are flow diagrams of example techniques for determining a parameter related to PD treatment based on a signal generated by a sensor of a catheter of a PD system.

DETAILED DESCRIPTION

Figure 1:
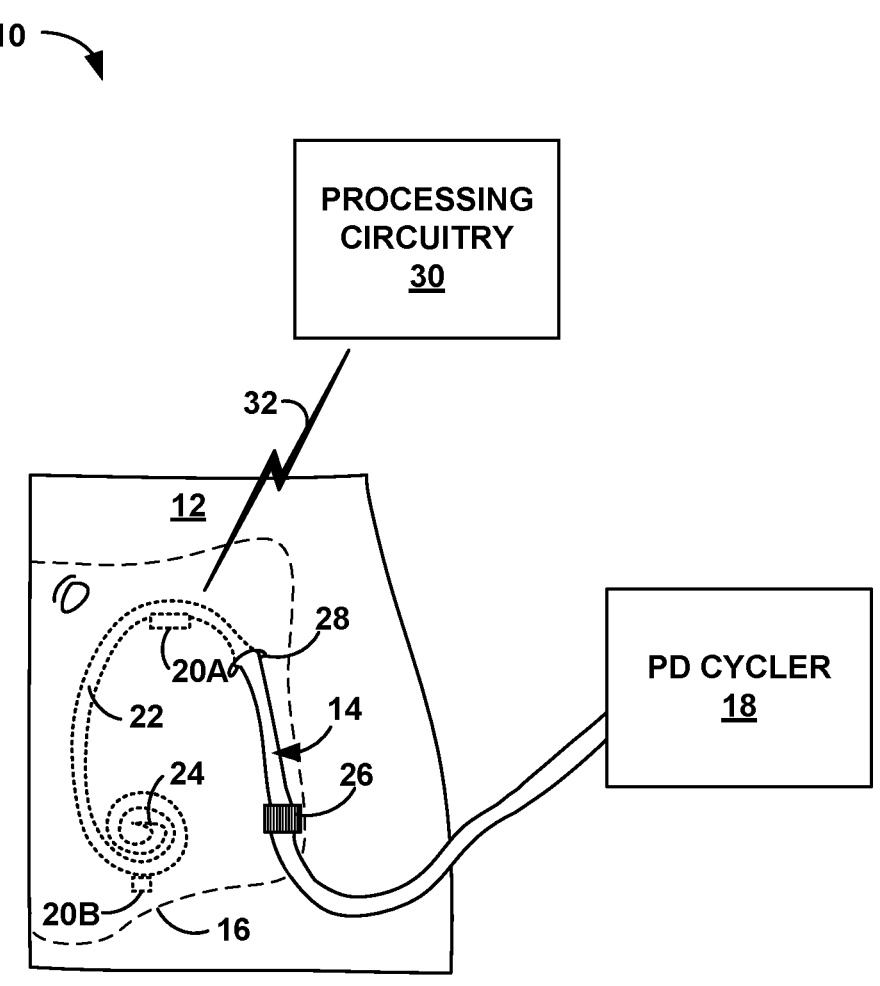
FIG. 1 is a diagram illustrating an example PD system configured to provide a patient with PD treatment.

Unless defined otherwise, all technical and scientific terms used generally have the same meaning as commonly understood by one of ordinary skill in the art.

The articles "a" and "an" are used to refer to one or more than one (e.g., at least one) of the grammatical object of the article. For example, "an element" means one element or more than one element.

An "alert" or a "notification" refers to any audio, visual, or tactile notification (or combinations thereof), such as an indication of a particular state of a system or patient.

The term "at least" refers to no less than or at the minimum. For example, "at least one" could be one or any numbers more than one.

A "blockage" of a catheter may refer to a reduced flow of fluid through the catheter, e.g., through a lumen of the catheter.

A "bolus" of a fluid may refer to volume of fluid.

A "catheter" is a fluid delivery conduit, such as a tubular member, configured to be inserted into a body of a patient. A catheter defines at least one lumen through which fluids may be introduced into and removed fluids from a patient. In some cases, medical devices can also be introduced into the patient or removed from the patient via a lumen of a catheter.

A "catheter body" may be an elongated structure of a catheter, e.g., an elongated tubular body, and may define one or more lumens of the catheter.

A "channel" may be a recess defined by a surface and may not be a through-opening.

A "characteristic" of a signal (e.g., a pressure signal) may include a time domain characteristic or a frequency domain characteristic. Example time domain characteristics include an amplitude of the signal (e.g., a mean, median, peak, or lowest instantaneous or average amplitude for a predetermined period of time), a frequency of the signal, a pattern or trend in the time domain signal over time, or the like. Example frequency domain characteristics include a peak, median, average or lowest power level of the signal within one or more predetermined frequency bands, a trend or pattern in the frequency domain characteristics within one or more predetermined frequency bands over time, or the like.

"Communication" can refer to, for example, a wired or wireless link between two components, such as an electrical connection, an optical connection, or the like.

The terms "comparing," "compare," or "comparison" can refer to, for example, determining the differences, if any, between two values or parameters.

A "concentration" and "solute concentration" can refer to, for example, an amount of a solute dissolved in a given amount of a solvent.

A "conductivity sensor" can refer to, for example, any component including circuitry, the component capable of measuring the electrical conductance or the electrical resistance of a fluid.

A "cover" described herein may cover (e.g., extend over) a channel defined by a catheter.

A "cycle" or "peritoneal dialysis cycle" can refer to, for example, the infusion of dialysate into a peritoneal cavity of a patient, a dwell period of the dialysate within the peritoneal cavity of the patient, and the removal of the dialysate from the peritoneal cavity of the patient following the dwell period. The process of filling and then draining the peritoneal cavity can also be referred to as an "exchange." The number, length, and timing of "cycles" or "exchanges" are non-limiting. For example, Continuous Ambulatory Peritoneal Dialysis (CAPD) and Continuous Cycling Peritoneal Dialysis (CCPD) may occur on different schedules, but the process of filling and then draining the peritoneal cavity can be referred to as "cycles" for both CAPD and CCPD. As such, the term "cycle" or "exchange" may refer to any particular dialysis schedule or type of dialysis.

A "dialysate" can refer to, for example, a fluid infused into a peritoneal cavity of a patient for PD treatment.

A "dwell period" or "dwell time" can refer to, for example, the amount of time elapsed between infusion of dialysate into a patient and drainage of the dialysate out of the patient.

An "effluent fluid" can refer to, for example, a fluid removed from a peritoneal cavity of a patient that includes a dialysate and any waste products removed from the patient.

An "electrical conductor" may include a structure configured to enables a flow of charge, such as, but not limited to, electrically conductive wire or the like.

The terms "fluidly connectable," "fluidly connected," "fluid connection" "fluidly connectable," or "fluidly connected" can refer to, for example, the ability to pass fluid, gas, or mixtures thereof from one point to another point. The two points can be within or between any one or more of compartments, modules, systems, and components, all of any type.

A "fluid parameter" includes any sensed parameter of a fluid, including temperature, pressure, concentration, color, or any other characteristic.

The term "fluid volume removed" or "fluid removal volume" can refer to, for example, the net volume of fluid removed from a patient during a PD cycle. The fluid removal volume is equal to the difference between the amount of dialysate infused into a patient and the amount of effluent removed from the patient with full draining.

"Historical information" can refer to information previously obtained and/or analyzed. For example, historical information may include dialysis parameters previously used and the resulting patient parameters or dialysis results from the use of such dialysis parameters.

An "impairment" of a catheter may include, for example, an obstruction of the catheter due to partially or fully blocking of an opening of the catheter, a blockage in a lumen of the catheter, or a presence of a kink in the catheter.

An "impedance sensor" includes sensing circuitry configured to generate an electrical signal indicative of an impedance of an electrical path, e.g., between electrodes of the impedance sensor. Processing circuitry may receive the electrical signal from the impedance sensor and determine an impedance value or other electrical parameter value that indicates the impedance of the electrical path.

"Infusing" or to "infuse" a fluid can refer to the movement of dialysate into a peritoneal cavity of a patient.

An "intraperitoneal pressure" is a pressure within a peritoneal cavity.

A "membrane of a peritoneal cavity," a "peritoneal membrane," and a "peritoneum" can refer to a lining of a peritoneal cavity of a patient.

A "memory" of a device may comprise any non-transitory memory, such as random access memory (RAM), read only memory (ROM), non-volatile RAM (NVRAM), programmable read only memory (PROM), erasable programmable read only memory (EPROM), electronically erasable programmable read only memory (EEPROM), or flash memory.

The term "monitoring" or to "monitor" can refer to determining a status of a system or patient.

An "osmotic agent" can refer to a substance dissolved in water capable of driving a net movement of water by osmosis across a semi-permeable membrane due to concentration differences of the osmotic agent on each side of the semi-permeable membrane.

An "osmotic agent concentration" can refer to the amount of an osmotic agent dissolved in a fluid per unit of volume.

A "patient" or "subject" ordinarily refers to a human patient. However, in other examples, "patient" or "subject" may refer to other mammalian or non-mammalian, non-human patients. The patient can be an apparently healthy individual, an individual with a patient condition that adversely affects a health of the patient, or an individual being treated for a patient condition.

"Peritoneal dialysis" (PD) or "peritoneal dialysis treatment" can refer to a therapy wherein a dialysate is infused into the peritoneal cavity of a patient, which serves as a natural dialyzer. In general, waste components diffuse from a patient's bloodstream across a peritoneal membrane into the dialysate via a concentration gradient. Excess fluid in the form of plasma water flows from the patient's bloodstream across the peritoneal membrane into the dialysate via an osmotic gradient. Once the infused dialysate has remained in the peritoneal for a dwell period, the fluid is removed. The cycle can be repeated for several cycles each day or as needed.

A "peritoneal dialysis cycler" or "cycler" can refer to components, including circuitry, for movement of fluid into and out of the peritoneal cavity of a patient.

A "peritoneal dialysis session" can refer to a set of peritoneal dialysis cycles performed over a time period as part of ongoing therapy. A peritoneal dialysis session can last a day or more, and can include any number of cycles.

A "peritoneum" refers to a lining of the abdominal cavity in a patient, or a membrane of the peritoneal cavity of the patient.

A "predetermined threshold" can refer to a value for a parameter, set before analysis, to which the analyzed parameter can be compared. Whether the analyzed parameter is greater than or less than the predetermined threshold can direct or cause some action to be taken.

A "pressure of a fluid" or "fluid pressure" can refer to a force exerted by a fluid.

A "pressure sensor" can refer to any component, including circuitry, capable of determining the force exerted by a fluid.

"Processing circuitry" can include one or more microprocessors, digital signal processors (DSPs), application specific integrated circuits (ASICs), field programmable gate arrays (FPGAs), programmable logic circuitry, or the like, either alone or in any suitable combination. In general, a processor may comprise any suitable arrangement of hardware (e.g., circuitry), alone or in combination with software and/or firmware, to perform the various techniques described herein and attributed to the processing circuitry.

A "sensor" can refer to component including circuitry and configured to determine one or more states of one or more variables in a system.

A "signal" generated by a sensor described herein includes an electrical signal, or another type of signal configured to transfer information.

"Sodium sieving" can refer to the movement of water from outside a peritoneal cavity of a patient into a dialysate in the peritoneal cavity of the patient without the movement of one or more solutes. For example, water may move across the peritoneum (e.g., via an aquaporin) into the dialysate while sodium is unable to move across the peritoneum into the dialysate.

A "solute" is a substance dissolved in, or intended to be dissolved in, a solvent.

A "solute concentration" refers to a concentration of a solute within a fluid.

A "trend" or "trending" can refer to changes in values for one or more parameters over time.

"Ultrafiltration" refers to a fluid removed from a patient during PD. An "ultrafiltrate transfer efficiency" can refer to the volume and rate that fluid is removed from a patient during a cycle, taking into account all dialysis parameters.

An "ultrafiltration volume" can refer to the net amount of fluid removed from a patient during a dialysis session.

Devices, systems, and techniques for monitoring a peritoneal dialysis (PD) system and related patient parameters are described herein. A PD system includes a PD cycler and at least one catheter, which defines at least one lumen through which the PD cycler delivers (e.g., infuses) a dialysate into a peritoneal cavity of a patient and through which the PD cycler removes an effluent fluid from the peritoneal cavity. The catheter may be a percutaneous catheter that is configured to be introduced into the peritoneal cavity of the patient to extend from inside the peritoneal cavity to outside of the patient's body through an exit site in the patient's abdomen. In some examples, the same catheter or the same lumen of a catheter is used for both the introduction of the dialysate into the peritoneal cavity and the removal of the effluent fluid from the peritoneal cavity. In other examples, however, different catheters or different lumens of a catheter may be used for the introduction of the dialysate into the peritoneal cavity and the removal of the effluent fluid from the peritoneal cavity. In some examples, the catheter may remain inserted in the peritoneal cavity of the patient at all times, even when the catheter is not connected to the PD cycler to facilitate treatment.

A catheter described herein includes a plurality of sensors configured and positioned to generate respective outputs indicative of the same or different parameters related to the PD treatment, which may be used to monitor the efficacy of PD treatment provided by a PD system, titrate a given PD prescription, and/or gain a broader overview of the PD system. For example, the sensors can include a pressure sensor configured to generate a pressure signal indicative of a pressure in a catheter lumen and/or or in a peritoneal cavity of a patient, and an impedance sensor configured to generate an impedance signal indicative of an impedance of the system in response to a fluid within the lumen of the catheter or external to the catheter. The impedance is referred to herein as an impedance in the catheter lumen and/or in the peritoneal cavity. Processing circuitry of a device is configured to receive the sensor output and determine the parameter related to the PD treatment.

The parameter related to PD treatment can include, for example, a catheter patency status or a peritoneal hemodynamic status. A catheter patency status (also referred to herein as a catheter status) may be indicative of a catheter being impaired. The catheter may be subject to issues that can affect the ability of the catheter to deliver a dialysate or remove an effluent fluid from the peritoneal cavity of the patient. Impairment of the catheter may include, for example, an obstruction of the catheter due to tissue ingrowth that partially or fully blocks an opening of the catheter, a blockage in a lumen (e.g., from a clot) of the catheter, or a presence of a kink in the catheter, any of which may result in reduced flow through the catheter or otherwise reduce the ability of the catheter to deliver a fluid into the patient or remove a fluid from the patient. A peritoneal hemodynamic status can include, for example, an indication of whether an excess or otherwise abnormal or unexpected amount of fluid is present within the peritoneal cavity, a physiological pressure or a non-physiologic pressure change in the peritoneal cavity, a relative change in an amount of fluid or a physiological pressure in the peritoneal cavity, or any combination thereof. In some examples, a PD system is configured to present a peritoneal hemodynamic status by at least providing an indication of that a parameter of PD treatment (also referred to herein as a PD prescription) should be modified (e.g., a concentration or a volume of ultrafiltration).

The information relating to the PD patient or the PD system provided by the one or more sensors may enable the patient or a clinician to evaluate, observe trends, determine an efficacy of the PD treatment, diagnose an issue that may affect the efficacy of the PD, and/or adjust one or more parameters of the PD treatment in a responsive manner.

FIG. 1 is a diagram illustrating an example PD system 10 configured to provide patient 12 with PD treatment. PD system 10 includes a catheter 14, which is illustrated as extending into a peritoneal cavity 16 of patient 12, and a PD cycler 18. Catheter 14 includes at least two sensors 20A, 20B configured to generate an output that is indicative of a parameter related to the PD treatment. The output is primarily referred to herein as an electrical signal, but can include other signals in other examples. Patient 12 ordinarily will be a human patient. In some cases, however, PD system 10 may be applied to other mammalian or non-mammalian, non-human patients.

PD cycler 18 is configured to deliver a dialysate into peritoneal cavity 16 via catheter 14. The dialysate remains in peritoneal cavity 16 for a dwell period, which has a duration that is intended to, but may not always be, sufficient for the exchange of waste products across a peritoneum of patient 12 to take place. In some such examples, PD cycler 18 may be disconnected from catheter 14 during the dwell period. In other examples, however, PD cycler 18 remains connected to catheter 14 during the dwell period. After the dwell period, PD cycler 18 removes fluid from peritoneal cavity 16. The fluid drained from peritoneal cavity 16 can be referred to as an effluent fluid, which contains the dialysate and the waste products removed from the blood of patient 12.

In some examples, the waste products may be removed by the dialysate due to a concentration gradient, e.g., due to the concentration of an osmotic agent in the dialysate, created in peritoneal cavity 16 when peritoneal cavity 16 is filled with the dialysate, which drives ultrafiltration and convective solute removal. The dialysate may include water, and dextrose or other sugars, salt, electrolytes, ions, and/or minerals as the osmotic agent. In some examples, the dialysate is dextrose-based, e.g., includes dextrose as the osmotic agent. Examples of dextrose-based dialysates include, but are not limited to, Dianeal available from Baxter Healthcare Corporation of Deerfield, IL and Delflex® available from Fresenius Medical Care of Waltham, MA In other examples, the dialysate may be characterized in having relatively low amounts of glucose degradation products (GDPs) and/or having a neutral pH (e.g., a pH of or close to 7). Examples of such dialysates include, but are not limited to, Physioneal available from Baxter Healthcare Corporation of Deer Field, IL, balance available from Fresenius Medical Care of Waltham, MA, and bicaVera® available from Fresenius Medical Care of Waltham, MA In yet other examples, dialysates may be icodextrin-based, such as Extraneal available from Baxter Healthcare Corporation of Deer Field, IL, or amino acid-based, such as Nutrineal™ available from Baxter Healthcare Corporation of Deer Field, IL.

In order to deliver the dialysate into peritoneal cavity 16 and remove the effluent fluid from peritoneal cavity 16, PD cycler 18 is connected to catheter 14, such as via an adapter 26, which provides the necessary mechanical connection between catheter 14 and PD cycler 18 to establish fluid communication therebetween. Catheter 14 may be any fluid delivery conduit capable of being inserted into peritoneal cavity 16 and connected to PD cycler 18 to facilitate PD treatment of patient 12. Catheter 14 defines an inner lumen 22 through which fluid may flow from PD cycler 18 to peritoneal cavity 16 and from peritoneal cavity 16 to PD cycler 18. Inner lumen 22 terminates at a distal opening, which can be at a distal-most end 24 of catheter 14, as shown in FIG. 1, and/or along a sidewall proximal to the distal-most end of catheter 14. Catheter 14 may be inserted into patient 12 via an exit site 28, and be configured to remain in patient 12 on a long-term basis, with a portion of catheter 14 remaining within peritoneal cavity 16 and a portion of catheter 14 residing outside of patient 12.

Catheter 14 can have any suitable configuration. For example, the portion of catheter 14 that remains within peritoneal cavity 16 may be straight or curvilinear, such as coiled (e.g., pig-tailed) as shown in FIG. 1. In some examples, a distal portion of catheter 14 has a swan neck (e.g., a curved portion 40, shown in FIGS. 2 and 3, curved up to about 180 degrees), which may help position catheter 14 at exit site 28 as intended. Catheter 14 has any suitable length for accommodating PD treatment. For example, catheter 14 may be between about 57 cm and about 62 cm in length (e.g., from adapter 26 to a distal-most end of catheter 14 within peritoneal cavity 16), and may be between about 2.5 mm and about 3.5 mm in diameter. In other examples, other shapes, sizes (e.g., length or diameter), and/or configurations may be used. An example of catheter 14 includes, but is not limited to, the Argyle™ Peritoneal Dialysis Catheter available from Medtronic, Inc. of Minneapolis, MN.

Sensors 20A, 20B are each positioned in inner lumen 22 of catheter 14 or external to inner lumen 22 and are each configured to generate a signal indicative of one or more parameters related to PD treatment provided by PD cycler system 10. For example, sensors 20A, 20B may be configured to sense a respective parameter of a fluid within inner lumen 22 or external to catheter 14, e.g., within peritoneal cavity 16. In examples described herein, sensor 20A includes a pressure sensor configured to generate a pressure signal indicative of a pressure of a fluid within inner lumen 22 or external to catheter 14 (e.g., an intraperitoneal pressure) and sensor 20B includes an impedance sensor configured to generate an impedance signal indicative of an impedance of an electrical path within inner lumen 22 or external to catheter 14, e.g., in peritoneal cavity 16. Thus, sensor 20A can also be referred to as a pressure sensor 20A and sensor 20B can also be referred to as an impedance sensor 20B. The fluid can be a dialysate, an effluent fluid, other bodily fluids, or any combination thereof.

The impedance signal may be indicative of a characteristic of a fluid in inner lumen 22 or external to catheter 14. Example characteristics can include, for example, a presence of a fluid, a relative volume of a fluid, an electrical conductivity of a fluid, or any combination thereof.

Although illustrated as two sensors in FIG. 1, in some examples, system 10 may include more than two sensors, such as three sensors or four or more sensors. Additionally, or alternatively, system 10 can include only one sensor configured to sense more than one parameter. For brevity, sensors 20A, 20B will be described with respect to generating a signal indicative of a parameter of a "fluid" in lumen 22, where the "fluid" may refer to a clean dialysate delivered to the peritoneal cavity as an effluent fluid, or where the parameter is indicative of a fluid in the peritoneal cavity 16, or other bodily fluids of patient 12. In addition, although FIG. 1 illustrates an example in which sensors 20A, 20B are positioned on a portion of catheter 14 that is in peritoneal cavity 16 when catheter 14 is inserted properly inserted in the patient, in other examples, sensor 20A and/or sensor 20B or another sensor of catheter 14 can be positioned on a portion of catheter 14 but remains inside of peritoneal cavity 16 (distal to exit site 28) or alternatively outside the peritoneal cavity 16 (proximal to exit site 28, but still part of catheter 14.

Figure 4:
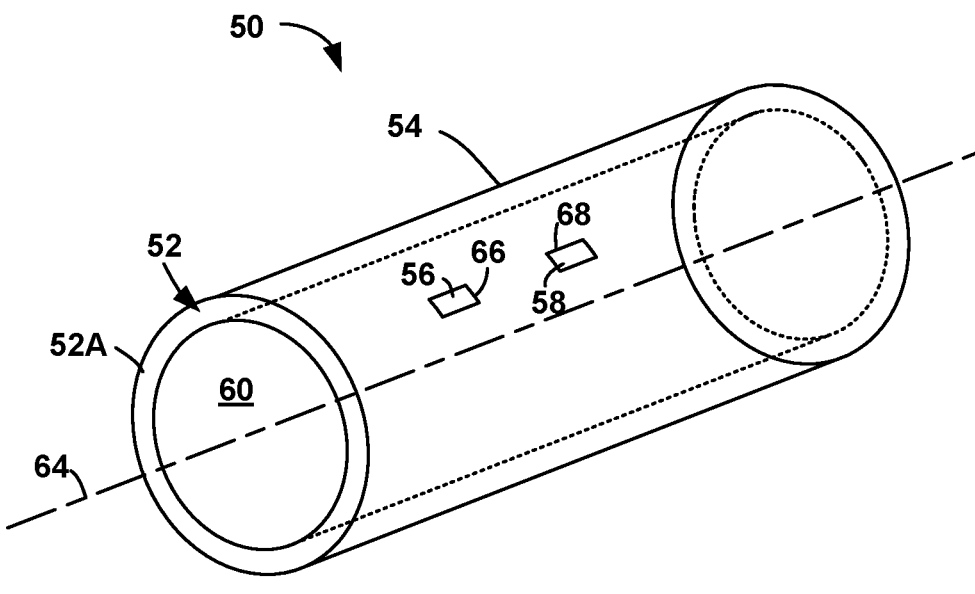
FIG. 4 is a conceptual perspective view of a part of an example catheter, which includes a catheter body defining a channel and an outer cover covering the channel (leaving the sensor exposed to the peritoneal cavity).
Figure 5:
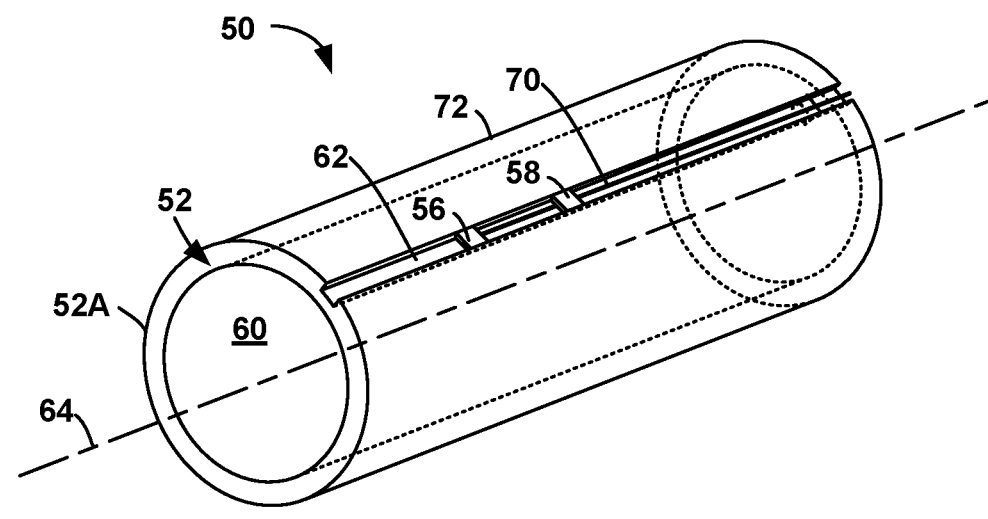
FIG. 5 is a conceptual perspective view of the catheter of FIG. 4, but illustrates the outer cover removed from the catheter.
Figure 6:
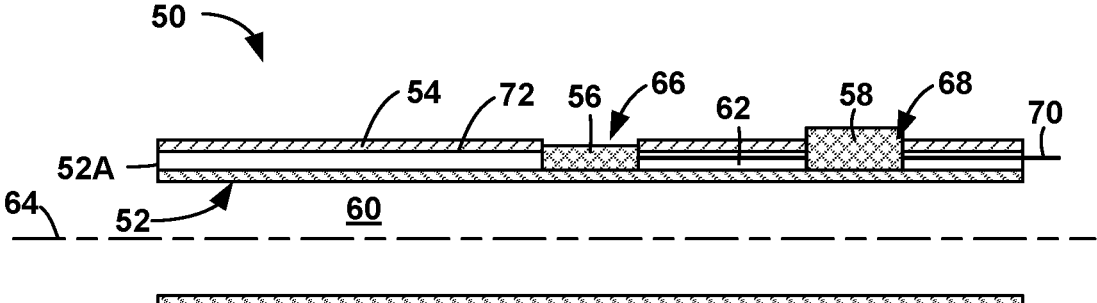
FIG. 6 is a conceptual cross-sectional view of the catheter of FIG. 4, where the cross-section is taken along a longitudinal axis of a catheter body of the catheter.
Figure 7:
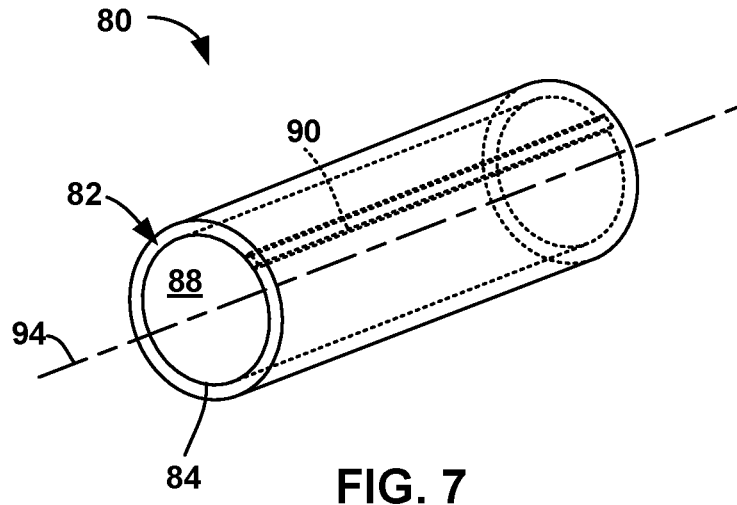
FIG. 7 is a conceptual perspective view of a part of an example catheter, which includes a catheter body defining a channel and an inner cover covering the channel.
Figure 8:
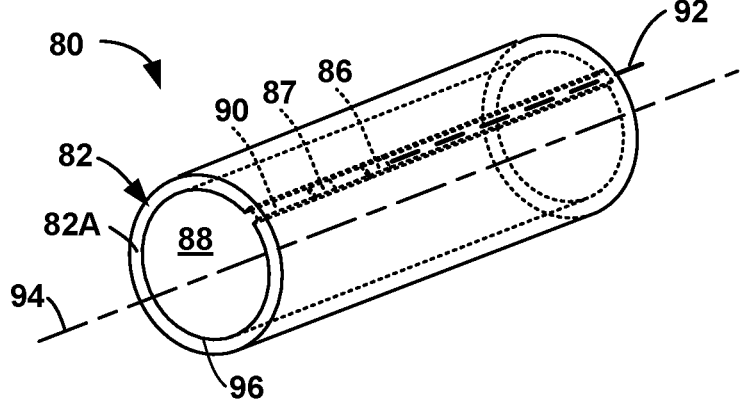
FIG. 8 is a conceptual perspective view of the catheter of FIG. 7, but illustrates the inner cover removed from the catheter and sensors in the channel defined by the catheter body.
Figure 9:
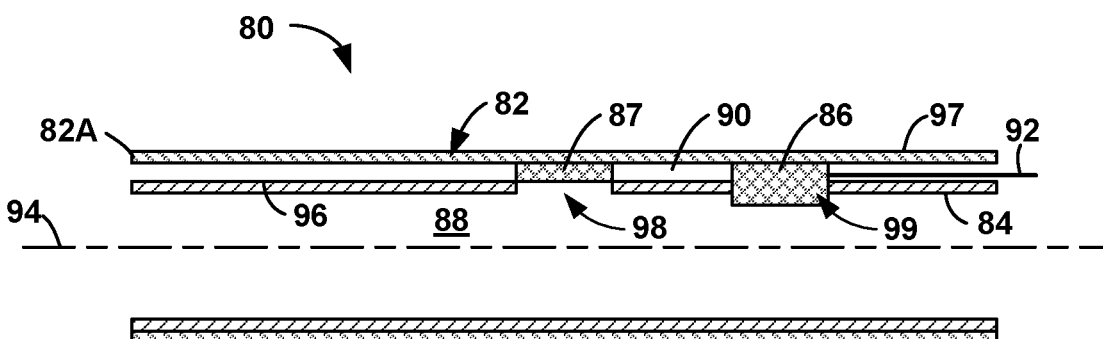
FIG. 9 is a conceptual cross-sectional view of the catheter of FIG. 7, where the cross-section is taken along a longitudinal axis of a catheter body of the catheter.

Sensors 20A, 20B are mechanically connected to catheter 14 using any suitable technique. In some examples, one or both sensors sensor 20A, 20B are adhered to catheter 14, thermally bonded to catheter 14, or welded to catheter 14. As discussed with reference to FIGS. 4-10, in some examples, a wall of catheter 14 can define a channel in which one or both sensors 20A, 20B are positioned, and in which electrical conductors that electrically connect one or both sensors 20A, 20B to processing circuitry 30 are positioned. The channel can be, for example, a recess (e.g., a groove) and may not be a through-opening. Sensors 20A, 20B can be positioned in the same channel or in different channels defined by catheter 14. The channels can be outwardly facing and defined in an outer wall of catheter 14, as shown in FIGS. 4-6 or can be inwardly facing and open to inner lumen 22, as shown in FIGS. 7-9. In some examples, the channel defined by catheter 14 can be covered by a cover, which is configured to prevent fluid from entering the channel. In some examples, the cover may define an opening that is aligned with sensor 20A and/or 20B, and, therefore, exposes the respective sensor 20A and/or 20B to an environment (e.g., inner lumen 22 or peritoneal cavity 16) to sense. In other examples, the cover may cover one or more of the sensors 20A, 20B and the sensors can be configured to sense the respective parameter through the cover.

As another example, one or both sensors 20A and/or 20B may be embedded within a wall of catheter 14, rather than place in a channel defined by catheter 14. In some examples, one or both sensors 20A and/or 20B are fixed to catheter 14 such that the sensor cannot move relative to catheter 14. In other examples, one or both sensors 20A and/or 20B may be connected to catheter 14 in a manner that enables the sensor to move relative to catheter 14, e.g., may be mechanically connected to catheter 14 via a flexible connection. In examples in which one or both sensors 20A and/or 20B are located within lumen 22 of catheter 14, the respective sensor and/or the channel defined by catheter 14 may be sized such that the sensor does not impede the flow of the dialysate or the effluent fluid through lumen 22. In examples in which one or both sensors 20A and/or 20B are located outside of lumen 22, e.g., along an outer surface of catheter 14, the respective sensor and/or the channel defined by catheter 14 may be sized such that the sensor does not hinder implantation of catheter 14 in peritoneal cavity 16.

PD system 10 includes processing circuitry 30, which is configured to receive an output (e.g., an electrical signal) generated by sensors 20A, 20B and determine information about PD system 10 and/or patient 12 based on the sensor output. The information about PD system 10 can include, for example, one or more of a catheter patency status or a peritoneal status, such as information indicating the presence of fluid in or inner lumen 22 of catheter 14 or in peritoneal cavity 16, respectively, or a characteristic of the fluid (e.g., an impedance of the fluid). The determination of such information about PD system 10 or patient 12 may be used to adjust the PD treatment delivered by PD cycler 18 to help improve the efficacy of the PD treatment or otherwise improve the patient experience, observe trends relating to the PD treatment; or the like.

Processing circuitry 30 may include any one or more microprocessors, DSPs, ASICs, FPGAs, programmable logic circuitry, or the like, either alone or in any suitable combination. The functions attributed to processing circuitry 30, as well as other processors described herein, may be embodied as firmware, hardware, software or any combination thereof.

In some examples, processing circuitry 30 can be part of PD cycler 18, while in other examples, processing circuitry 30 can be part of a different device, such as a clinician computer that is located near PD cycler 18 or remotely located (e.g., more than 50 feet away) from PD cycler 18. Although not shown in FIG. 1, processing circuitry 30 may be part of a device that includes additional components, such as, but not limited to, a memory, a telemetry module that includes circuitry to facilitate communication between processing circuitry 30 and another component, such as sensors 20A, 20B, and a power source. Similarly, although not shown in FIG. 1, in some examples, one or both sensors 20A and/or 20B can include its own processor, a memory, a telemetry module, and/or a power source.

Sensors 20A and/or 20B are configured to transmit respective electrical signals indicative of sensed parameters (e.g., pressure and/or impedance) related to PD system 10 or to patient 12, or both, to processing circuitry 30. Processing circuitry 30 is configured to transmit signals to control sensors 20A and/or 20B, such as to request sensed parameter information from the particular sensor 20A, 20B, to control when sensor 20A, 20B actively senses a parameter related to PD system 10, or the like.

Sensors 20A, 20B and processing circuitry 30 are configured to communicate with each other using any suitable communication technique and via any suitable wired or wireless communication channels. In the example shown in FIG. 1, sensors 20A, 20B communicate with processing circuitry 30 via wireless signals 32. Processing circuitry 30 and one or both sensors 20A, 20B may communicate using any of a variety of local wireless communication techniques, such as radio frequency (RF) communication according to the 802.11 or Bluetooth® specification sets, infrared (IR) communication according to the IRDA specification set, or other standard or proprietary telemetry protocols, or via remote telemetry such as, for example, via a local area network (LAN), wide area network (WAN), public switched telephone network (PSTN), or cellular telephone network.

Processing circuitry 30 may also communicate with another computing device via a wired or wireless connection using any of any of the local or remote wireless communication techniques discussed with respect to communication between sensors 20A, 20B and processing circuitry 30. Processing circuitry 30 may also communicate with other computing devices via exchange of removable media, such as magnetic or optical disks, memory cards, or memory sticks.

Under the control of processing circuitry 30 or another processor of PD system 10, sensors 20A, 20B each sense one or more parameters related to PD treatment provided by PD cycler 18, and generate a respective signal indicative of the respective sensed parameter. Processing circuitry 30 is configured to receive the signals from sensors 20A, 20B at any suitable rate, such as continuously or intermittently at any suitable frequency. In some examples, a clinician can provide input to processing circuitry 30, e.g., via a user interface, such as user interface 112 shown in FIG. 11, that indicates the frequency with which sensors 20A, 20B should sense the pressure or impedance, and/or the rate at which sensors 20A, 20B transmits the pressure signal or the impedance signal, respectively, to processing circuitry 30. The sensing frequency can be selected using any suitable technique. In some cases, such as for patients that have recently started PD treatment or PD treatment by a specific system 10, system 10 can be configured such that processing circuitry 30 receives the signals from sensors 20A, 20B at a higher frequency compared to patients that have been receiving PD treatment or PD treatment by a specific system 10 for a longer period of time. This may enable, for example, a clinician to better track the efficacy of PD system 10 and modify the PD prescription (e.g., dwell time, a concentration of osmotic agents in the dialysate delivered to the patient, or the like) and/or the position of catheter 14 within peritoneal cavity 16 to try to achieve better results.

Example frequencies (timing) with which processing circuitry 30 receives the signals from sensors 20A, 20B can include, for example, once every 30 minutes or every hour. In some cases, processing circuitry 30 receives the signals from sensors 20A, 20B at different frequencies, e.g., if a parameter sensed by one sensor 20A or 20B is expected to change at a different rate than the parameter sensed by the other sensor 20B or 20A.

In some examples, sensors 20A, 20B may provide information relating to the adequacy, parameters, and/or function of PD system 10 (e.g., PD cycler 18 and/or catheter 14) to a clinician and/or patient 12. In turn, the clinician may be able to adjust the PD prescription to better fit the specific needs of patient 12. For example, the clinician may adjust the dwell period, the number of cycles of the PD treatment given in a particular time period (e.g., one day or a week), the type of dialysate used for PD, the concentration of the osmotic agent in the dialysate, the volume of the dialysate delivered to peritoneal cavity 16 of patient 12, or the like. In some examples, PD system 10 stores the information generated by sensors 20A, 20B over time, which enables the clinician to monitor one or more parameters of PD system 10 over time and gain a better understanding of the overall function of PD system 10, the overall adequacy of the PD treatment provided by PD system 10, changes in the condition of patient 12 over time, or the like.

Processing circuitry 30 is configured to determine information about the PD treatment system and/or patient 12, such as information about peritoneal cavity 16 of patient 12, catheter 14, or a fluid, based on a characteristic of signals generated by sensor 20A, 20B. As used herein, a characteristic of signals generated by sensors 20A, 20B may include a time domain characteristic or a frequency domain characteristic. Example time domain characteristics include an amplitude of the signal (e.g., a mean, median, peak, or lowest instantaneous or average amplitude for a predetermined period of time), a frequency of the signal generated by the sensor 20A, 20B (e.g., a mean, median, peak, or lowest frequency), a pattern or trend in the time domain signal over time, or the like. Example frequency domain characteristics include a peak, median, average or lowest power level of the signal within one or more predetermined frequency bands, a trend or pattern in the frequency domain characteristics within one or more predetermined frequency bands over time, or the like. In some examples, sampling rates for sensed values is over a 60-minute window with daily averages calculated using 24-hour samples for each sensed parameter. Smoothed data can then be used for assessing changes over time in addition to instantaneous changes against set thresholds as described below.

In some examples, to detect a particular patient state or state of PD system 10 (e.g., a catheter obstruction), processing circuitry 30 may compare a characteristic of at least one signal generated by one or both sensors 20A, 20B to a predetermined threshold value. For example, processing circuitry 30 may determine whether a characteristic of the signal is greater than, less than, or equal to a predetermined threshold value. Additionally, or alternatively, processing circuitry 30 may determine at least one trend of a characteristic of the signal generated by one or both sensors 20A, 20B over time and compare the trend to a template (e.g., a waveform template) to detect a particular catheter 14 status or a peritoneal cavity 16 status. In some examples, processing circuitry 30 may determine that a particular catheter 14 status or peritoneal cavity 16 status is detected in response to determining the characteristic of the signal is increasing over time, decreasing over time, fluctuating over time, or remaining approximately the same over time.

In some examples, in addition to, or as an alternative to, comparing a characteristic of a signal to a predetermined threshold value or determining at least one trend of the characteristic over time, processing circuitry 30 may determine an absolute value of a sensed parameter using at least one characteristic of signals generated by one or both sensors 20A, 20B. In these examples, processor may determine catheter 14 status, peritoneal cavity 16 status, or other state of PD system 10 based on a comparison between the determined value to a predetermined threshold value or based on a comparison of a trend in the value over time to a template. Thus, pressure values determined by processing circuitry 30 based on a pressure signal generate by sensor 20A can be an absolute pressure value or a relative pressure value (e.g., indicating a change in pressure between time points). Likewise, impedance values determined by processing circuitry 30 based on an impedance signal generate by sensor 20B can be an absolute impedance value or a relative impedance value.

The one or more predetermined threshold values and/or one or more templates with which processing circuitry 30 determines a parameter related to PD treatment provided by PD system 10 can be stored within a memory of system 10, such as within a memory 78 (FIG. 11) of a device that includes processing circuitry 30, within a memory of one or both sensors 20A, 20B, within PD cycler 18 or another device, or any combination thereof. The one or more predetermined threshold values and/or one or more templates can be determined by processing circuitry 30 or by another device based on historical PD cycles of patient 12 or a group of patients including or not including patient 12. The one or more predetermined threshold values and/or one or more templates can indicate, for example, an acceptable level of a particular parameter that indicates PD treatment provided by PD system 10 is efficacious or is at least consistent with past PD treatment provided to patient 12. Thus, the threshold values and/or templates may be from a previously generated signal, such as from a previous PD cycle, and/or may be based on previously generated signals, such as a mean or median of previously generated signals.

In some examples, the thresholds or trends may be determined from one PD cycle to another, or from one PD session to another, where a session includes multiple PD cycles. In other examples, the stored values or data may be based on population data or patient history. As another example, the stored values or data may be related to ideal values or data, such as, for example, a pressure of a fluid in inner lumen 22 when catheter 14 is known to not be impaired, impedance values indicative of an amount of fluid in peritoneal cavity 16 from an adequate PD cycle, or the like. In this way, the predetermined threshold values, trends, and/or other values may be based on values and/or data representing a relatively unimpaired catheter patency status and/or a desired status of peritoneal cavity 16.

In some examples, the one or more predetermined threshold values and/or one or more templates with which processing circuitry 30 determines a parameter related to PD treatment provided by PD system 10 may also have an auto-adaptive component. For example, processing circuitry 30 or other processing circuitry of another device may analyze stored values of a given parameter (e.g., pressure or impedance) in relation patient activity, patient meals, and/or other variables that may impact the efficacy of treatment provided by PD system 10. Such adaptive thresholds may be automatically updated by processing circuitry 30 or manually updated by a clinician based on the patient's activities of daily living and/or by time averaged most recent historical data (e.g., daily average pressures, daily average impedance values, and the like).

Regardless of whether processing circuitry 30 compares a characteristic of a signal to a predetermined threshold value, determines at least one trend of the characteristic over time, determines a value using at least one characteristic of a signal, or combinations thereof, processing circuitry 30 determines information about the PD treatment system and/or patient 12 based on the signals generated by sensors 20A, 20B.

In some examples, processing circuitry 30 is configured to determine a status of catheter 14 based on the signals generated by one or both sensors 20A, 20B, which can include signals indicative of at least one of a pressure in inner lumen 22 of catheter 14 or an impedance of system 10 and indicative of a characteristic (e.g., presence, volume, electrical conductivity, or any combination thereof) of fluid within inner lumen 22. The status of catheter 14 can be, for example, a blockage of catheter 14 that adversely affects an ability of catheter 14 to efficiently deliver fluid into peritoneal cavity 16 or remove fluid from peritoneal cavity 16 may become impaired. For example, a presence of a blockage within lumen 22 of catheter 14, a kink in catheter 14, tissue in-growth around an opening to lumen 22 of catheter 14, fibrosis formation around catheter 14, a shift in the position of catheter 14, or the like may result in the reduction of fluid flow through a lumen of catheter 14. Processing circuitry 30 is configured to determine a status of catheter 14, such as by detecting an obstruction of catheter 14 or an encapsulation of the distal opening of catheter 14 that may adversely impact the fluid flow through inner lumen 22 of catheter 14, by at least comparing characteristic of one or both signals generated by sensors 20A, 20B to a predetermined threshold value, determining at least one trend of the characteristic over time, or both. Processing circuitry 30 may use any suitable characteristic of the signals generated by one or both sensors 20A, 20B to compare to the predetermined threshold value and/or to determine a trend of the characteristic to determine a status of catheter 14. Further, any of the parameters (e.g., pressure and impedance) discussed herein may be used alone or in combination to detect a status of catheter 14.

In some examples, processing circuitry 30 determines that catheter 14 is impaired (e.g., inner lumen 22 is obstructed) in response to determining a pressure of fluid within inner lumen 22 of catheter 14 is greater than or equal to a predetermined threshold value or has increased over time. For example, processing circuitry 30 may determine that the status of catheter 14 is impaired if the pressure of the fluid in inner lumen 22 has increased by about 1.25 times for a given flow rate indicated by PD cycler 18. In another example, processing circuitry 30 determines that catheter 14 is impaired in response to determining an impedance sensed within an electrical path in inner lumen 22 of catheter 14 is greater than or equal to a predetermined impedance value. The impedance of the electrical path in inner lumen 22 less than or equal to the predetermined impedance value can indicate, for example, that there is a kink or other obstruction proximal to the location of the impedance sensor 20A or 20B that is limiting or even preventing fluid from flowing from PD cycler 18 to the location of the impedance sensor.

In response to detecting an obstruction of a lumen of catheter 14, blockage of a distal catheter opening, or another catheter status that may adversely impact the efficacy of PD provided by PD cycler 18, processing circuitry 30 may generate a notification that notifies a clinician or patient 12 that processing circuitry 30 has detected the adverse catheter status. The notification, as well as other notifications described herein, can be delivered to the patient or the clinician via any suitable user interface, such as via user interface 112 (FIG. 11) of a device that includes processing circuitry 30, via a light or other visible indication on catheter 14 or PD cycler 18, or the like. The notification can include a visible, audible, and/or somatosensory notification.

Determination of the status of catheter 14 by PD system 10 may help a clinician and/or patient intervene relatively quickly in order to address an issue that may be adversely impacting the efficacy of the PD treatment, such as an obstruction. For example, in response to receiving the alert, a clinician or processing circuitry 30 may control PD cycler 18 to provide a bolus of fluid through inner lumen 22 of catheter 14 in an attempt to pulse and/or move catheter 14 within peritoneal cavity 16 and/or dislodge the obstruction of catheter 14. In some examples, processing circuitry 30 may subsequently control one or both sensors 20A, 20B to generate another signal indicative of a parameter of the fluid in catheter 14 so that processing circuitry 30 can determine if the obstruction was minimized or even eliminated by the fluid bolus. In other examples, the obstruction or other condition of catheter 14 may be resolved in another way.

In examples in which processing circuitry 30 is configured to determine status of peritoneal cavity 16 or the PD treatment based on signals generated by one or both sensors 20A, 20B, the respective one or more sensors 20A, 20B is configured to generate a signal indicative of at least one of a pressure in lumen 22 of catheter 14, a pressure external to catheter 14 within peritoneal cavity 16, or an impedance of system 10 and indicative of an amount or electrical conductivity of fluid within peritoneal cavity 16. The pressure and impedance can be absolute values ore relative values (e.g., a change in the pressure or impedance between time points).

In some examples, a sudden drop in pressure inside lumen 22 of catheter 14 indicated by the signal generated by a sensor 20A could indicate enough of the dialysate in peritoneal cavity 16 has been removed. Thus, in some examples, in response to detecting a change in pressure over time greater than or equal to a predetermined threshold value, processing circuitry 30 can directly or indirectly control PD cycler 18 to reduce the amount of fluid PD cycler 18 removes from peritoneal cavity 16 (e.g., stopping the removal of effluent fluid or significantly decreasing the amount of effluent fluid removed). Processing circuitry 30 can also notify a clinician (e.g., via presenting information via user interface 112 shown in FIG. 11) of the sudden drop in pressure in lumen 22 during a dwell period so that the clinician can shorten the dwell period or other PD prescription parameters for future dialysis treatment sessions (of patient 12). In these example ways, processing circuitry 30 can control the functionality of PD cycler 18 based on an output from sensor 20A and/or 20B.

In some examples, processing circuitry 30 can use a pressure signal generated by sensor 20A and indicative of pressure external to the portion of catheter 14 within peritoneal cavity 16 in combination with an impedance signal generated by sensor 20B and indicative of an amount of fluid within peritoneal cavity 16 to determine a prescription for PD treatment provided by PD cycler 18. For example, in some examples, processing circuitry 30 can determine that there is fluid build-up in peritoneal cavity 16 in response to determining the pressure signal indicates pressure has been rising in peritoneal cavity 16, even without active PD treatment (e.g., in between PD treatment cycles), and an impedance signal indicates that has been a corresponding drop in impedance. Processing circuitry 30 can be configured to detect these conditions by, for example, detecting a pressure in peritoneal cavity 16 greater than or equal to a predetermined threshold pressure value and/or a change in pressure in peritoneal cavity 16 over time in greater than or equal to a first predetermined threshold rate of change, and by detecting an impedance less than or equal to a predetermined threshold impedance value and/or a change impedance in peritoneal cavity 16 over time in greater than or equal to a second predetermined threshold rate of change.

In response to determining that there is fluid build-up in peritoneal cavity 16, processing circuitry 30 may modify an ultrafiltration volume used by PD cycler 18 during the current PD treatment session, if applicable, or during a future PD treatment session. The ultrafiltration volume refers to the net amount of fluid removed from peritoneal cavity 16 during a PD session. Processing circuitry 30 may determine the ultrafiltration volume for a particular PD cycle of PD cycler 18 based on the difference between the volume of dialysate introduced into peritoneal cavity 16 and the volume of the effluent fluid. A decrease in the volume of ultrafiltrate generated during a cycle of PD cycler 18 over time may indicate a reduced health state of the peritoneum of patient 12. Adjusting the ultrafiltration volume impacts the amount of effluent fluid PD cycler 18 removes from peritoneal cavity 16 during the treatment cycle. For example, a higher volume of ultrafiltration results in more effluent fluid being removed from peritoneal cavity 16. Thus, in some examples, in response to determining that there is fluid build-up in peritoneal cavity 16 based on the pressure and impedance signals generated by sensors 20A, 20B, processing circuitry 30 controls PD cycler 18 to increase the ultrafiltration volume during a current or a next PD treatment session in order to remove more fluid from peritoneal cavity 16.

Processing circuitry 30 or another device can determine the thresholds used to detect the fluid build-up in peritoneal cavity 16 using any suitable technique. In some examples, processing circuitry 30 or another device monitors pressure and impedance signals generated by sensor 20A or 20B over a trial period and determines how much effluent fluid was removed from peritoneal cavity 16. The volume of effluent fluid (ultrafiltration volume) can be correlated with pressure and impedance values to generate patient-specific thresholds used by processing circuitry 30 to control PD cycler 18. For example, processing circuitry 30 may determine that when a certain volume of effluent fluid was removed from peritoneal cavity 16, a certain pressure (or range of pressure values) was sensed by sensor 20A in peritoneal cavity 16 during some time period prior to the removal of the effluent fluid. In addition to or instead of the aforementioned technique, in some examples, processing circuitry 30 or another device monitors pressure and impedance signals generated by sensor 20B over a trial period and receives input from patient 12 associating patient comfort levels with the sensed pressure and impedance in peritoneal cavity 16. In these examples, the sensed pressure and impedance values indicated by the output from sensors 20A, 20B can then be applied by processing circuitry 30 as the threshold pressure value and the threshold impedance value, respectively.

In some examples, processing circuitry 30 can use an impedance signal generated by sensor 20B and indicative of an impedance of the system and indicative of fluid within peritoneal cavity 16 to set the prescription for a PD treatment session, with or without the pressure information discussed above. For example, the impedance signal can provide information about a level of sodium in an effluent fluid, which in turn may help determine an effectiveness of the transport of waste products across the peritoneum and/or the health of the peritoneum of patient 12. For example, the electrical conductivity of fluid in peritoneal cavity 16 during a PD treatment session may increase as the level of sodium in the effluent concentration increases, which may be indicative of the amount of sodium that was able to be removed from the blood of patient 12. In some examples, processing circuitry 30 determines that a PD prescription, e.g., the concentration of osmotic agent in a dialysate or a frequency of PD treatment sessions, should be modified in response to determining the electrical conductivity of fluid in peritoneal cavity 16 is less than or equal to a predetermined threshold impedance value or has decreased over time by greater than or equal to a threshold amount. The determination of the electrical conductivity of fluid in peritoneal cavity 16 can be determined, for example, at the end of the dwell period and before PD cycler 18 removes the effluent fluid from peritoneal cavity 16, or during a dwell period.

In some examples, the electrical conductivity being less than or equal to a predetermined threshold value or decreasing over time by greater than or equal to a threshold amount may be indicative of sodium sieving, which in some cases, may be relating to inadequate PD treatment due to an insufficient amount (e.g. concentration) of osmotic agent, too much osmotic agent in a dialysate, an insufficient amount of effluent fluid being removed from peritoneal cavity 16 by PD cycler 18 during a PD treatment cycle, too much effluent fluid being removed from peritoneal cavity 16 by PD cycler 18 during a PD treatment cycle, or the like. A dialysate introduced into peritoneal cavity 16 via catheter 14 by PD cycler 18 includes an osmotic agent, which helps create a concentration gradient to remove waste products from the blood of patient 12 during a PD cycle.

In some examples, in response to determining that a PD prescription should be modified based on the impedance signal generated by one or both sensors 20A, 20B, processing circuitry 30 may generate a notification that notifies a clinician or patient 12 that the PD prescription should be modified. In addition to or instead of generating the notification, in some examples, processing circuitry 30 or another processor of system 10 automatically adjusts or recommends changes of one or more parameters of the PD cycler 18 in response to determining that a PD prescription should be modified based on the impedance signal. For example, if processing circuitry 30 determines that the sensed impedance indicative of an amount of fluid within peritoneal cavity 16 is less than or equal to predetermined threshold impedance value or is decreasing over time by greater than or equal a threshold amount, then processing circuitry 30, alone or with the aid of a clinician, may adjust the dwell period, dialysate type, or osmotic agent concentration, number of PD treatment cycles per unit time, or other parameters relating to the PD treatment for patient 12. PD system 10 can enable the clinician to continue monitoring information relating to the PD treatment system or patient 12 following the adjustments, such as, for example, to determine how any adjustments made to the PD treatment are affecting the treatment of patient 12.

Figure 11:
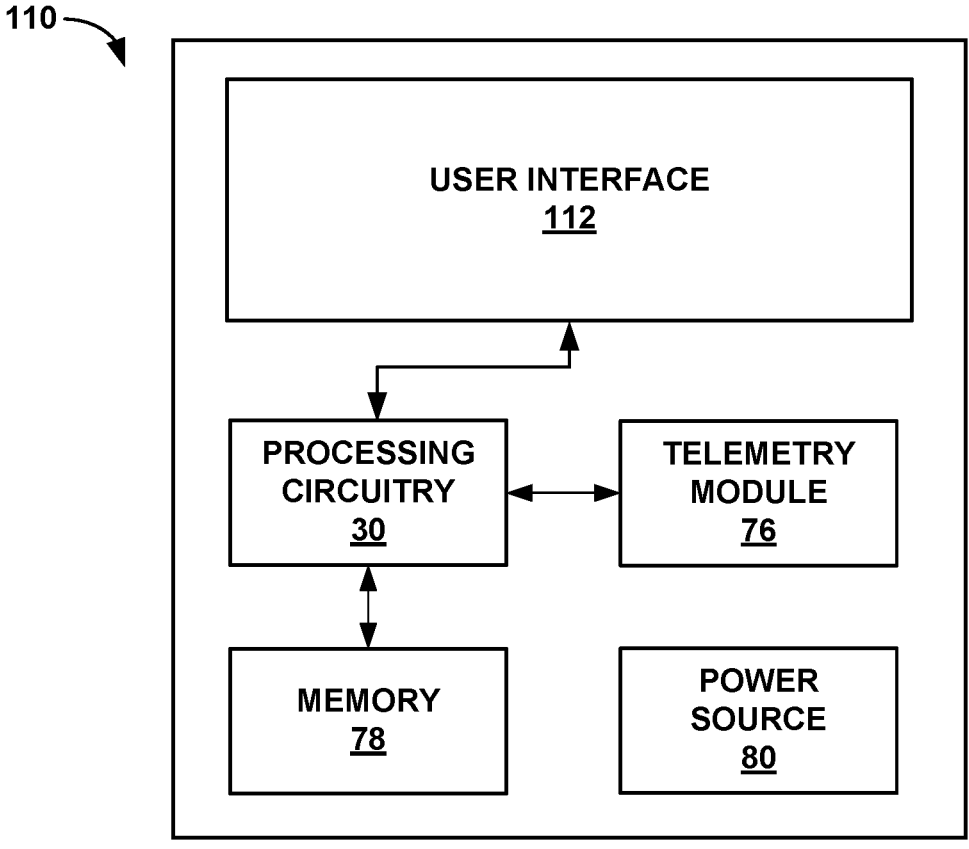
FIG. 11 is a block diagram illustrating an example device configured to receive a signal from a sensor and determine information about a patient or a PD treatment of the patient based on the signal.

In addition to one or more threshold values or templates, processing circuitry 30 may store, e.g., in memory 78 shown in FIG. 11 or a memory of another device, historical parameters, characteristics of parameters, trends, or values (e.g., from a previous cycle, based on population data, based on patient history, or the like) in a memory of system 10. For example, processing circuitry 30 may store a pressure with which PD cycler 18 delivers a dialysate into peritoneal cavity 16 of patient 12, a flow rate of the fluid dialysate, a pressure within catheter 14 at a given fluid flow rate of the dialysate, a determined or threshold intraperitoneal pressure, determined impedance values, and the like.

Figure 2:
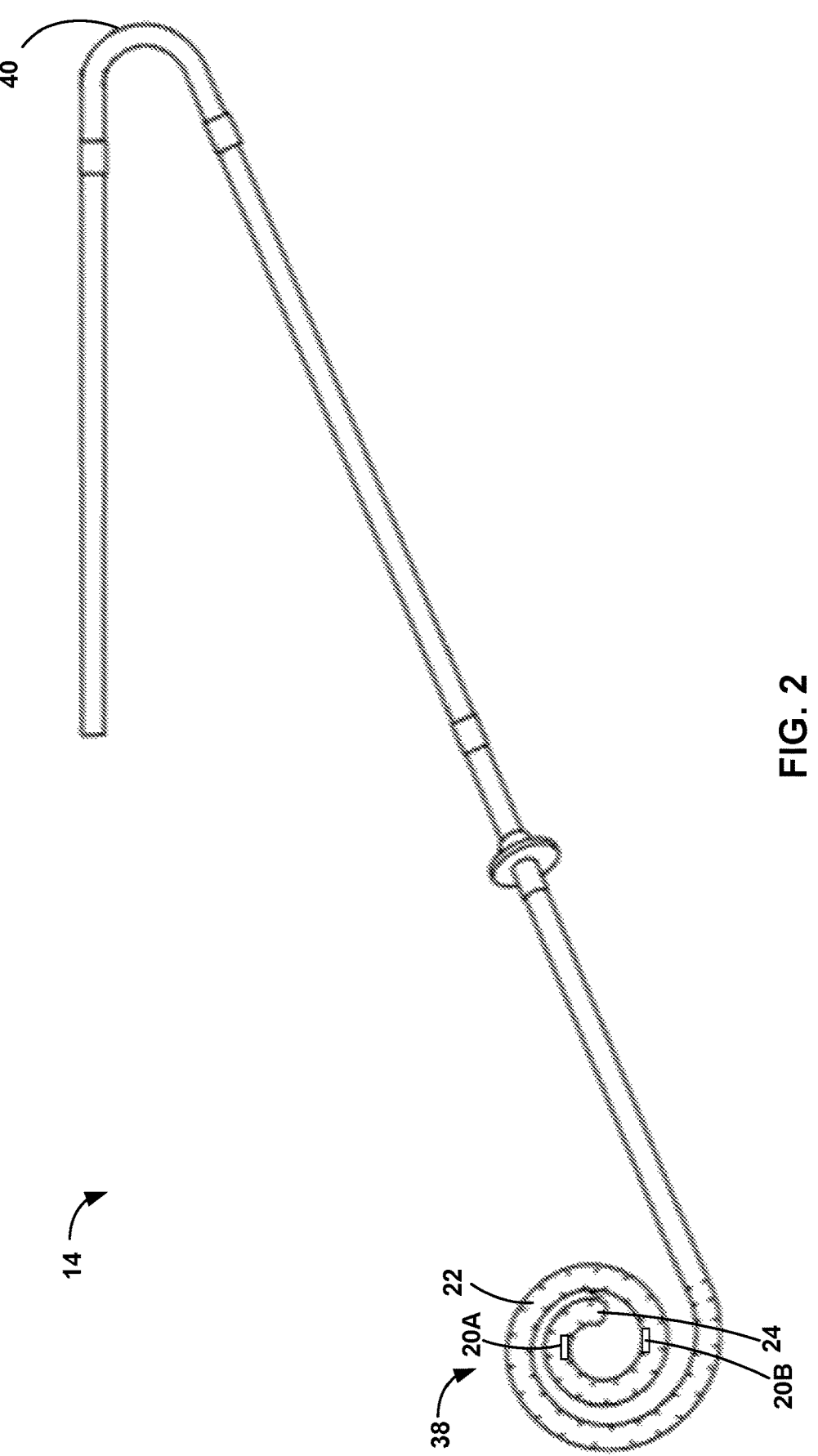
FIG. 2 is a conceptual perspective view of an example PD catheter that can be used in the PD system of FIG. 1, and illustrates a pressure sensor and an impedance sensor in a lumen of a catheter.

FIG. 2 is a conceptual illustration of an example of catheter 14, and illustrates pressure sensor 20A and impedance sensor 20B in lumen 22 defined by catheter 14. In the example shown in FIG. 2, catheter 14 includes a coiled (e.g., pig-tailed) shaped distal portion 38 that is configured to be positioned within peritoneal cavity 16 when catheter 14 is used to provide patient 12 with PD. In other examples, however, distal portion 38 can have another suitable shape, such as, but not limited to, a straight shape or a different curvilinear shape. In addition, catheter 14 is shown to have a preformed bend 40, which may help decrease stress on exit site 28 (FIG. 1) during use of catheter 14. Although sensors 20A, 20B are shown as being located near a distal-most end 24 of catheter 14 on curved distal portion 38, in some examples, one or both sensors 20A, 20B may be located more proximally in other examples, such as a more proximal portion of lumen 22 that is configured to remain within peritoneal cavity 16 during use of catheter 14 or is configured to be outside of peritoneal cavity 16 during use of catheter 14. In addition, one or both sensors 20A, 20B can be positioned on a portion of catheter 14 that is not curved.

In the example shown in FIG. 2, pressure sensor 20A configured to generate a pressure signal indicative of a pressure of a fluid within lumen 22 of catheter 14. Pressure sensor 20A, as well as other pressure sensors described herein, can include circuitry configured to generate a signal correlated to the pressure imposed on the pressure sensor, and, therefore, indicative of the force exerted by the fluid within lumen 22. In some examples, pressure sensor 20A, as well as other pressure sensors described herein, may include a pressure transducer, which may be embodied as any pressure-sensitive transducer, including, but not limited to, piezoelectric, capacitive, electromagnetic, piezoresistive, optical, or potentiometric transducers. In other examples, pressure sensor 20A may include a different type of pressure sensor. Pressure sensor 20A has a relatively low profile and can include, for example, a microelectromechanical systems (MEMS) pressure sensor.

In the example shown in FIG. 2, impedance sensor 20B is configured to generate a signal indicative of an impedance of a fluid in lumen 22. The impedance can be indicative of, for example, a presence or an absence of a dialysate or effluent fluid in lumen 22 and/or a concentration of a substance in a fluid in lumen 22, which can indicate whether a clinician should modify a concentration of an osmotic agent in a dialysate PD cycler 18 delivers to peritoneal cavity 16 during a PD cycle.

In some examples, impedance sensor 20B, as well as other impedance sensors described herein, includes one or more of: a conductivity meter, a resistivity meter, a multimeter, or a voltmeter. In other examples, impedance sensor 20B may include a different type of electrical conductivity or electrical resistance sensor. In one example, impedance sensor 20B includes electrodes in lumen 22 and circuitry configured to generate a signal that changes as a function of the electrical conductance or the electrical resistance of a fluid in contact with the electrodes. For example, processing circuitry 30 may source an electrical signal, such as current, to one electrode of the impedance sensor, while another electrode of the impedance sensor sinks the electrical signal. Processing circuitry 30 may then determine the voltage between the electrodes, which is indicative an impedance of an electrical path through fluid in lumen 22 between the electrodes.

Although sensor 20A, 20B are shown as being located in lumen 22 in FIG. 2, in other examples, pressure sensor 20A and/or impedance sensor 20B can be located elsewhere on catheter 14 in addition to or instead of in lumen 22. For example, pressure sensor 20A and/or impedance sensor 20B may be located within lumen 22 in a portion of catheter 14 residing external to patient 12. As another example, pressure sensor 20A and/or impedance sensor 20B can be positioned an outer surface of catheter 14, as shown in FIG. 3, which illustrates another example of catheter 14.

In addition, although sensors 20A, 20B are shown as being located near a distal-most end 24 of catheter 14 on curved distal portion 38, in some examples, pressure sensor 20A and/or impedance sensor 20B may be located more proximally in other examples, but remains on a portion of catheter 14 that is within peritoneal cavity 16 during use of catheter 14. In some examples in which pressure sensor 20A is positioned external to lumen 22, pressure sensor 20A is configured to generate a pressure signal indicative of a pressure of a fluid external to catheter 14. For example, pressure sensor 20A can include circuitry configured to generate a signal indicative of the force exerted by the fluid on an external surface of catheter 14 within peritoneal cavity 16.

In examples in which impedance sensor 20B is positioned external to lumen 22, impedance sensor 20B is configured to generate an impedance signal indicative of an impedance of a fluid external to catheter 14 and in contact with sensor 20B, e.g., in peritoneal cavity 16. The impedance can be indicative of, for example, a presence or an absence of a dialysate in peritoneal cavity 16 and/or a concentration of a substance in a fluid in peritoneal cavity 16, which can indicate whether a clinician should modify a concentration of a dialysate delivered to peritoneal cavity 16 during a PD cycle.

Figure 3:
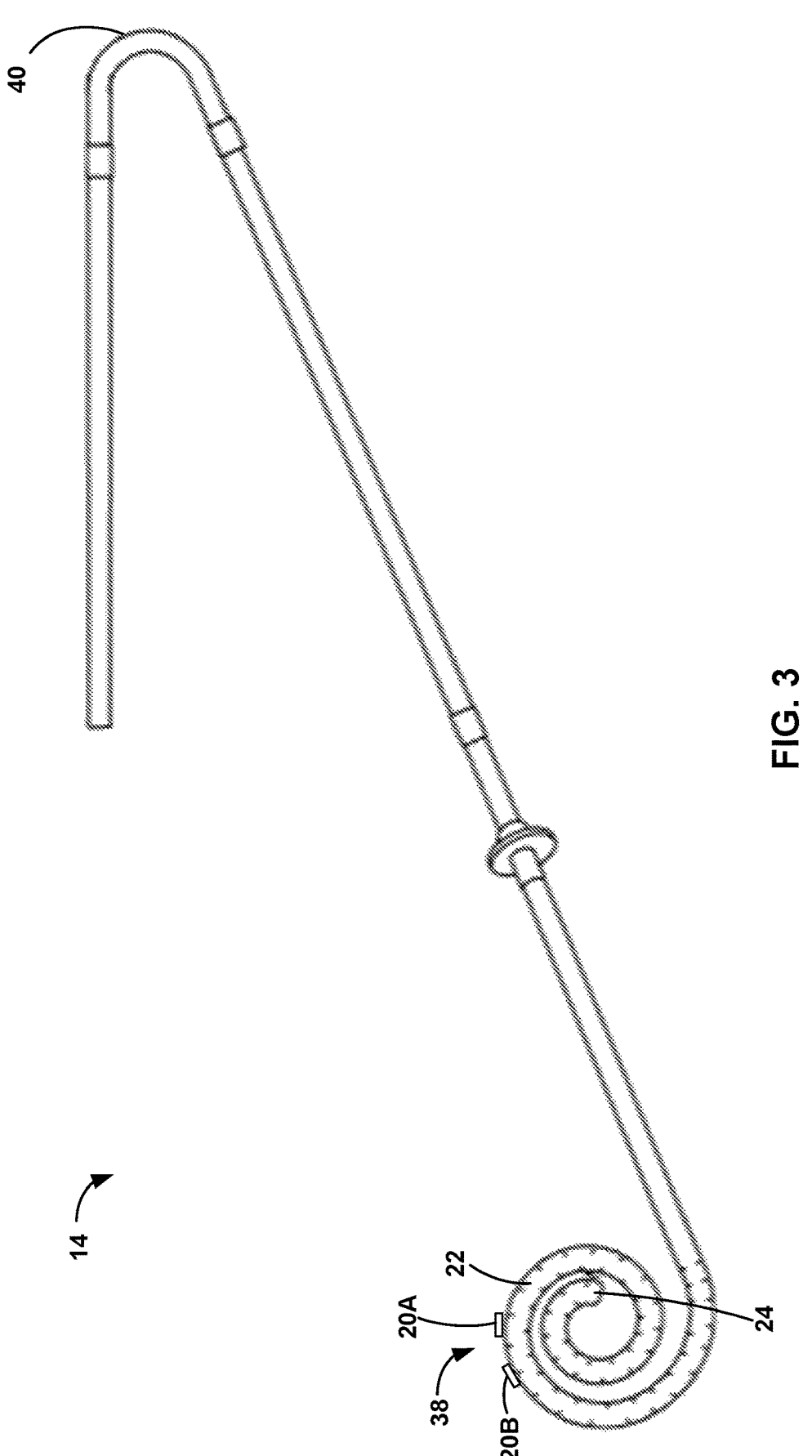
FIG. 3 is a conceptual perspective view of an example PD catheter that can be used in the PD system of FIG. 1, and illustrates a pressure sensor and an impedance sensor outside of a lumen of a catheter and configured to sense pressure and impedance, respectively, in a peritoneal cavity.

Although FIGS. 2 and 3 illustrate impedance sensor 20B proximal to pressure sensor 20A, in other examples, impedance sensor 20B can be positioned on catheter 14 distal to pressure sensor 20A. Further, catheter 14 can include more than one pressure sensor 20A and/or more than one impedance sensor 20B.

FIG. 4 is a conceptual perspective view of a part of a catheter 50, which includes an elongated catheter body 52 and an outer cover 54 positioned over and covering at least part of catheter body 52. FIG. 5 is a conceptual perspective view of the same part of catheter 50, but illustrates the outer cover 54 removed from catheter 50. FIG. 6 is a conceptual cross-sectional view of part of the catheter 50, where the cross-section is taken along longitudinal axis 64 of catheter body 52. Catheter body 52 defines inner lumen 60, through which PD cycler 18 delivers a dialysate to peritoneal cavity 16 and through which PD cycler 18 removes effluent fluid from peritoneal cavity 16. Catheter 50 and lumen 60 are examples of catheter 14 and lumen 22 discussed with reference to FIGS. 1-3, and sensors 56, 58 are examples of sensors 20A, 20B discussed with reference to FIGS. 1-3. For example, sensor 56 can include a pressure sensor and sensor 58 can include an impedance sensor.

As discussed above, one or more sensors of a catheter can be positioned on any suitable location on the catheter. In the example shown in FIGS. 4 and 5, sensors 56, 58 are positioned on an outer surface of catheter body 52 and, in particular, in a channel 62 defined by catheter body 52, as shown in FIG. 5. Channel 62 extends from an outermost surface 72 of catheter body 52 and radially inwards partially through a thickness of an outer wall of catheter body 52, where a thickness is measured in a direction orthogonal to longitudinal axis 64. Channel 62 does not extend all the way through the outer wall of catheter body 52 and, therefore, is not open to lumen 60. In some examples, as shown in FIG. 4, channel 62 terminates proximal to distal-most end 52A of catheter body 52. For example, channel 62 can terminate at a location that corresponds to a distal end of sensor 56, such that channel 62 does not distally extend beyond the distal-most sensor 56 and such that fluid is not able to enter channel 62 via an opening to channel 62 at a distalmost end 52A of catheter body 52. In other examples, as shown in FIG. 5, channel 62 extends to a distal-most end 52A of catheter body 52.

Outer cover 54 is positioned radially outward of catheter body 52 and is configured to partially cover channel 62. In the example shown in FIG. 4, outer cover 54 defines openings 66, 68 configured to align with sensors 56, 58, respectively, and expose the respective sensor 56, 58, when outer cover 54 covers channel 62. For example, both catheter body 52 and outer cover 54 may be tubular structures, and outer cover 54 can be configured to extend fully an outer perimeter of catheter body 52 (e.g., an outer perimeter being a circumference in examples in which catheter body 52 is circular in cross-section, the cross-section being taken in a direction orthogonal to longitudinal axis 64). In other examples, outer cover 54 can cover channel 62 (except for openings 66, 68 exposing channel 62) without extending fully an outer perimeter of catheter body 52. In other examples, outer cover 54 may cover one or more of the sensors 56, 58 and the one or more sensors 56, 58 can be configured to sense the respective parameter through outer cover 54.

Outer cover 54 can be formed from any suitable material, such as any suitable polymer or silicone. Example polymers include, but are not limited to, polyurethane, polyethylene, polyvinylchloride (PVC), ethylvinylacetate (EVA), polyethylene terephthalate (PET), thermoplastic elastomers (e.g., polyester), polyimide, polyamides (e.g., nylon), high density polyethylene (HDPE), low density polyethylene (LDPE), polypropylene, fluoropolymers (e.g., polyetryfluorehtylene (PTFE), fluorinated ethylene propylene (FEP), polysulfones, polyether block amide (e.g., PEBAX®, commercially available from Arkema Group of Colombes, France), or the like. Blends, alloys, mixtures, copolymers, block polymers, of these materials can also be used.

In some examples, outer cover 54 is formed from a material that is substantially impermeable (e.g., impermeable or nearly impermeable to the extent permitted by manufacturing tolerances) to fluids in peritoneal cavity 16, such that fluid is prevented from penetrating through outer cover 54 into channel 62 except where openings 66, 68 are located. Outer cover 54 is closely fit to outermost surface 72 of catheter body 52 such that a fluid that enters channel 62 via openings 66, 68 may not flow between catheter body 52 and outer cover 54. Outer cover 54 can be mechanically connected to catheter body 52 using any suitable technique, such as by heat-shrinking, which may eliminate the need for an adhesive to further mechanically connect outer cover 54 to catheter body 52. In addition to or instead of heat-shrinking, outer cover 54 can be adhered to catheter body 52 using a thermoset or a thermoplastic adhesive or via welding.

Because sensors 56, 58 are positioned in channel 62, sensors 56, 58 are recessed in an outer wall of catheter body 52. In some examples, one or both of the sensors 56, 58 are fully recessed, such that they do not protrude past an external surface of catheter 50. An example of a fully recessed sensor is shown in FIG. 6 with respect to sensor 56. In these examples, a depth of channel 62 (measured in a direction orthogonal to longitudinal axis 64) is equal to or greater than a thickness (measured in a direction orthogonal to longitudinal axis 64) of sensors 56, 58, such that sensors 56, 58 do not protrude past outermost surface 72 of catheter body 52 and/or outer cover 54. This may enable catheter 50 to maintain a relatively low profile, which can facilitate implantation of catheter 50 in peritoneal cavity 16. In other examples, one or both sensors 56, 58 are partially recessed in channel 62 such that when sensors 56, 58 are positioned in channel 62, at least one of the sensors 56, 58 extend past outermost surface 72 of catheter body 52 and, in some examples, an outermost surface of outer cover 54. An example of a partially recessed sensor is shown in FIG. 6 with respect to sensor 58. In these examples, a depth of channel 62 is less than the thickness of the partially recessed sensor. Sensors extending past outermost surface 72 of catheter body 52 might better enable the sensors 56, 58 to sense the respective extracatheter parameter, whether it be pressure or impedance, due at least in part to better exposure to the environment outside catheter body 52.

Channel 62 defined by catheter body 52 defines a space for sensors 56, 58, as well as one or more electrical conductors 70 that are configured to transmit signals generated by sensors 56, 58 to processing circuitry 30 either directly or indirectly via another device. Conductors 70 are positioned between catheter body 52 an outer cover 54. Thus, outer cover 54 helps to protect electrical conductors 70 from environmental contaminants, such as fluid, which can adversely impact the functionality of the electrical conductors 70. In some examples, all electrical conductors of catheter 50 are positioned between catheter body 52 an outer cover 54.

In other examples of catheter 50, one or both sensors 56, 58 may be configured to wirelessly communicate with processing circuitry 30, as shown in FIG. 1, in which case, no conductors 70 or fewer conductors 70 may be present in channel 62.

In other examples of catheters described herein, instead of or in addition to including a catheter body 52 defining channel 62 that extends from an outermost surface of catheter body 52 radially inwards, in some examples, a catheter can include a channel (also referred to herein as an "inner channel") along an interior surface of a catheter body, i.e., along a lumen, and one or more sensors can be positioned in the inner channel. An example of such a catheter 80 is shown in FIGS. 7-9. Catheter 80 that includes a catheter body 82, an inner cover 84, and sensors 86, 87.

Catheter body 82 defines an inner lumen 88 and an inner channel 90 that extends from an innermost surface 96 of catheter body 82 defining inner lumen 88 and radially outwards towards an outermost surface 72 of catheter body 82. FIG. 7 is a conceptual perspective view of a part of catheter 80 with sensors 86, 87 removed for a better view of inner channel 90, FIG. 8 is a conceptual perspective view of the same part of catheter 50 with inner cover 84 removed, but including sensors 86, 87 and an electrical conductor 92 in inner channel 90, and FIG. 9 is a conceptual cross-sectional view of part of the catheter 80, where the cross-section is taken in a direction parallel to longitudinal axis 94 of catheter body 82.

Electrical conductor 92 is configured to electrically connect sensor 86 to processing circuitry 30 (either directly or indirectly via another device) and is similar to electrical conductor 70 described with reference to FIGS. 4-6. In some examples, electrical conductor 70 or another similar electrical conductor electrically connects sensor 87 to processing circuitry 30. Electrical conductor 92 is positioned between catheter body 82 and inner cover 84, such that inner cover 84 can help protect electrical conductor 92 from environmental contaminants that may adversely impact the structural integrity of conductor 92. In some examples, all electrical conductors of catheter 80 are positioned between catheter body 82 and inner cover 84. In other examples of catheter 80, one or both sensors 86, 87 may be configured to wirelessly communicate with processing circuitry 30, as shown in FIG. 1.

An innermost surface 96 of catheter body 82 defines inner lumen 88, through which PD cycler 18 delivers a dialysate to peritoneal cavity 16 and through which PD cycler 18 removes effluent fluid from peritoneal cavity 16. Catheter 80 and lumen 88 are examples of catheter 14 and lumen 22 discussed with reference to FIGS. 1-3, and sensors 86, 87 are examples of sensors 20A, sensor 20B discussed with reference to FIGS. 1-3. In some examples of catheter 80, catheter 80 includes both sensors 86, 87 in inner channel 90, while in other examples, catheter 80 includes only one sensor 86 or 87 in inner channel 90. In addition, or instead, catheter body 82 can define an outer channel, e.g., like channel 62 shown in FIGS. 4-6, in which one or more additional sensors are positioned, such as sensors 56 and/or 58 discussed with reference to FIGS. 4-6. Thus, the features of catheters 50 (FIGS. 4-6) and catheter 80 (FIGS. 7-10) can be used in any suitable combination.

In the example shown in FIGS. 8 and 9, sensors 86, 87 of catheter 80 are positioned along an inner surface of catheter body 82 and, in particular, in inner channel 90 defined by catheter body 52. Channel 90 extends from innermost surface 96 of catheter body 82 and radially outwards partially through a thickness of a wall of catheter body 82, where a thickness is measured in a direction orthogonal to longitudinal axis 94. Channel 90 does not extend all the way through the wall of catheter body 82 and, therefore, is not open to an environment external to catheter body 82. Channel 90 is, however, open to inner lumen 88 of catheter body 82. In some examples, as shown in FIG. 7, channel 90 terminates proximal to distal-most end 82A of catheter body 82. For example, channel 90 can terminate at a location that corresponds to a distal end of the distal-most sensor 86, such that channel 90 does not distally extend beyond sensor 86 and such that fluid is not able to enter channel 90 via an opening to channel 90 at a distalmost end 82A of catheter body 82. In other examples, as shown in FIG. 8, channel 90 extends to a distal-most end 82A of catheter body 82.

Inner cover 84 is positioned radially inward of catheter body 82 and is configured to partially cover channel 90. Inner cover 84 defines openings 98, 99 configured to expose sensors 86, 87, respectively, when inner cover 84 covers channel 90, thereby enabling sensors 86, 87 to sense one or more characteristics (e.g., pressure and/or impedance) of a fluid within inner lumen 88. For example, both catheter body 82 and inner cover 84 may be tubular structures, and inner cover 84 can be configured to extend fully an inner perimeter of catheter body 82 (e.g., an outer perimeter being a circumference in examples in which catheter body 82 is circular in cross-section, the cross-section being taken in a direction orthogonal to longitudinal axis 94). In other examples, inner cover 84 can cover channel 90 (except for at openings 98, 99) without extending fully an inner perimeter of catheter body 82. In other examples, inner cover 84 may cover one or more of the sensors 86, 87 and the one or more sensors 86, 87 can be configured to sense the respective parameter through inner cover 84.

Inner cover 84 can be formed from any suitable material, such as any suitable polymer or silicone. Example materials described above for outer cover 54 can also be used for inner cover 84. In some examples, inner cover 84 is formed from a material that is substantially impermeable to fluids in peritoneal cavity 16, such that fluid is prevented from penetrating through inner cover 84 into inner channel 90 except where openings 98, 99 are located. Inner cover 84 is closely fit to innermost surface 96 of catheter body 82 such that a fluid that enters channel 90 via openings 98, 99 may not flow between catheter body 82 and inner cover 84. Inner cover 84 can be mechanically connected to catheter body 82 using any suitable technique, such as via an adhesive, welding, or the like.

Because sensors 86, 87 are positioned in inner channel 90, sensors 86, 87 are recessed in an outer wall of catheter body 82. In the example shown in FIG. 9, sensor 86 is fully recessed, such that it does not protrude past innermost surface 96 of catheter 80. In these examples, a depth of inner channel 90 (measured in a direction orthogonal to longitudinal axis 94) is equal to or greater than a thickness (measured in a direction orthogonal to longitudinal axis 94) of sensor 86, such that sensor 86 does not protrude past innermost surface 96 of catheter body 82 and/or inner cover 84. This may help minimize any adverse effects sensor 86 has on fluid flow within lumen 88. In other examples, sensor 86 is only partially recessed in inner channel 90 such that when sensor 86 is positioned in inner channel 90, sensor 86 extends into inner lumen 88. In the example shown in FIG. 9, sensor 87 is only partially recessed in inner channel 90, such that it extends into inner lumen 88.

Although FIGS. 4-9 illustrate example catheters 50, 80 in which sensors are positioned in channels 62, 90, respectively, defined by the catheter bodies 52, 82, in other examples, catheters described herein can include sensors embedded in a catheter body or attached to an outermost or innermost surface of the catheter body, rather than in a channel defined by the catheter body. In any of the examples, whether the sensor is in a channel, embedded in a catheter body, or otherwise attached to the catheter body, the sensor can include a material to help reduce protect the sensor from environmental factors. The material can be applied as a casing, a coating, embedded in the sensor, or any other suitable application. For example, the material include biocompatible materials such as silicones, parylenes (e.g., poly (p-xylene)-based polymers), antithrombogenic materials, platelet aggregation inhibitors, or the like. Example antithrombogenic materials or platelet aggregation inhibitors include, but are not limited to, 2-Methacryloyloxyethyl phosphorylcholine (MPC, available as LIPIDURE™ from NOF Corporation of Tokyo, Japan); PARYLENE C™, or PARYLENE HT™, both available from Specialty Coating Systems of Indianapolis, Indiana; BAYIVIEDIX™ available from Bayer AG of Leverkusen, Germany; BIOCOAT™ hyaluronic acid available from BioCoat, Inc. of Horsham, PA; or polyethylene oxide; heparin, heparin-like materials or derivatives, hirudin, H-Heparin, HSI-Heparin, albumin, phospholipids, streptokinase, tissue plasminogen activator (TPA), urokinase, hyaluronic acid, chitosan, methyl cellulose, poly(ethylene oxide), poly(vinyl pyrrolidone), endothelial cell growth factor, epithelial growth factor, osteoblast growth factor, fibroblast growth factor, platelet derived growth factor or angiogenic growth factor. The casing and/or coating may reduce thrombogenic surfaces of sensor.

Figure 10:
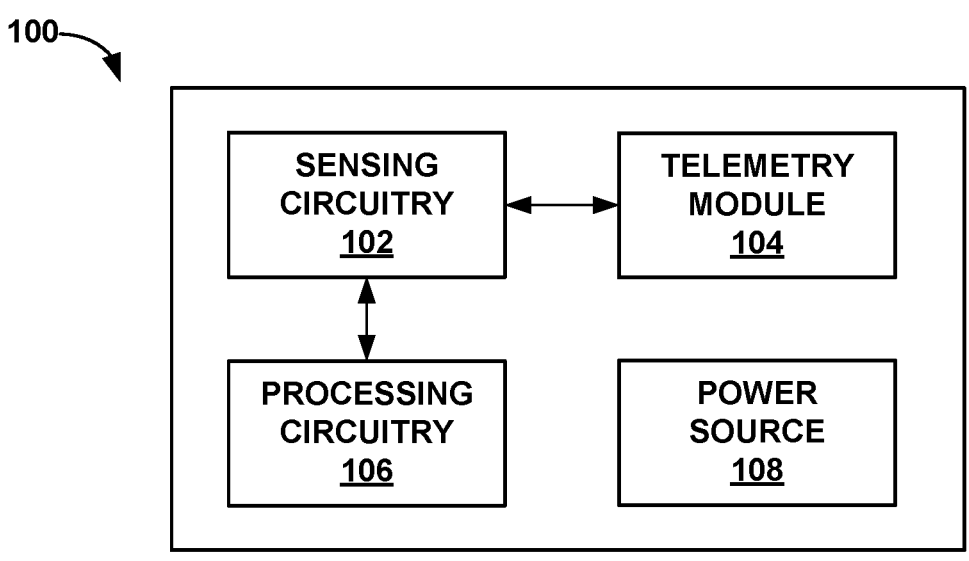
FIG. 10 is a block diagram illustrating an example sensor configured to generate a signal indicative of a parameter of a dialysate.

FIG. 10 is a block diagram illustrating an example sensor 100 configured to generate a signal indicative of a parameter indicative of one or more parameters related to PD treatment provided to the patient. Sensor 100 may any sensor described herein, such as sensor 20A or 20B of FIGS. 1 and 2, sensor 56 or 58 of FIGS. 4-6, or sensor 86 or 87 of FIGS. 7-9. Sensor 100 includes sensing circuitry 102, telemetry module 104, processing circuitry 106, and power source 108.

Processing circuitry 106 is configured to control sensing circuitry 102 to generate one or more signals indicative of one or more parameters of the fluid within catheter 14 or peritoneal cavity 16. For example, sensing circuitry 102 can include circuitry capable of generating a signal that changes as a function of a pressure, an electrical resistance, or an electrical conductivity of a fluid. In some examples, sensing circuitry 102 includes an electrical conductivity sensor, an electrical resistance sensor, pressure transducer, a piezometer, or a combination thereof. In other examples, sensing circuitry 102 may include other sensing capabilities.

In some examples, sensing circuitry 102 is configured to generate a signal indicative of a parameter of the fluid continuously. In other examples, sensing circuitry 102 is configured to generate the signal at a predetermined time interval, which may be determined by a clinician and input to processing circuitry 106 of sensor 100 via user interface 112, discussed with reference to FIG. 11. In yet another example, sensing circuitry 102 may be configured to generate the signal after sensor 100 receives a request from processing circuitry 30.

Processing circuitry 106 may include any processing circuitry, such as, for example, any one or more of a microprocessor, a controller, a DSP, ASIC, FPGA, or equivalent discrete or integrated logic circuitry. In some examples, processing circuitry may include multiple components, such as any combination of one or more microprocessors, one or more controllers, one or more DSPs, one or more ASICs, or one or more FPGAs, as well as other discrete or integrated logic circuitry. The functions attributed to processing circuitry described herein may be embodied as firmware, hardware, software or any combination thereof. Processing circuitry controls sensing circuitry 102 to generate one or more signals indicative of one or more parameters of a fluid within catheter 14 or peritoneal cavity 16, such as, but not limited to, a pressure signal or an impedance signal.

In some examples, processing circuitry 106 is configured to send the signal from sensing circuitry 102 to processing circuitry 30 (FIG. 1), e.g., via telemetry module 104. Other types of information may also be transmitted to processing circuitry 30, such as the timing of the generation of the signals. In other examples, processing circuitry may send the generated signal after being interrogated by processing circuitry 30 to send the signals.

Telemetry module 104 includes any suitable hardware, firmware, software or any combination thereof for communicating with another device, such as processing circuitry 30 (FIG. 1). Under the control of processing circuitry, telemetry module 104 may receive downlink telemetry from and send uplink telemetry to processing circuitry 30 with the aid of an antenna, which may be internal and/or external. Processing circuitry 106 may provide the data to be uplinked to processing circuitry 30 and the control signals for the telemetry circuit within telemetry module 104, e.g., via an address/ data bus. In some examples, telemetry module 104 may provide received data to processing circuitry via a multiplexer.

The various components of sensor 100 are coupled to power source 108, which may include a rechargeable or non-rechargeable battery. In some examples, a non-rechargeable battery may be selected to last for several years, while a rechargeable battery may be inductively charged from an external device, e.g., on a daily or weekly basis.

FIG. 11 is block diagram of an example device 110 including processing circuitry 30. Device 110 further includes user interface 112, telemetry module 114, memory 116, and power source 118. Device 110 may be a dedicated hardware device with dedicated software for functioning in accordance with the disclosed techniques. Alternatively, device 110 may be an off-the-shelf computing device running an application that enables device 110 to function in accordance with the disclosed techniques.

In some examples, a user may use device 110 to obtain information about a PD treatment of a patient. For example, such information may be used to adjust the PD treatment; diagnose and treat various conditions; observe trends relating to the PD treatment; improve the PD treatment, patient experience, and/or patient condition; or the like. The clinician may interact with device 110 via user interface 112, which may include display to present graphical user interface to a user, and a keypad or another mechanism for receiving input from a user.

Memory 116 may store instructions that cause processing circuitry 30 to provide the functionality ascribed to processing circuitry 30 and device 110 herein, and information used by processing circuitry 30 to provide the functionality ascribed to processing circuitry 30 and device 110 herein. For example, memory 116 may store one or more predetermined threshold values, characteristics of parameters, trends of parameters, trends of characteristics of parameters, values, and/or trends of values described herein. Additionally, or alternatively, memory 116 may store historical data or historical signals and/or trends of such historical data or signals. For example, memory 116 may store historical signals received from sensor 100 such that processing circuitry 30 is able to determine a trend over time in a characteristic of a parameter indicated by the signal, in accordance with the techniques of the disclosure.

Memory 116 may also store information that enables device 110 to communicate with and/or control sensor 100 (or any other sensor described herein), such as, when to generate a signal indicative of a parameter of fluid in catheter 14 or peritoneal cavity 16 or to send a generated signal to device 110. Memory 116 may comprise any suitable memory, such as RAM, ROM, NVRAM, PROM, EEPROM, flash memory, comprising executable instructions for causing the processing circuitry 30 to perform the actions attributed to it.

Device 110 may communicate wirelessly with sensor 100 (FIG. 10) or another device, such as using RF communication or proximal inductive interaction. This wireless communication is possible through the use of telemetry module 114, which may be coupled to an internal antenna or an external antenna. Telemetry module 114 may be similar to telemetry module 104 of sensor 100 (FIG. 10). Telemetry module 114 may also be configured to communicate with another computing device via wireless communication techniques, or direct communication through a wired connection. Examples of local wireless communication techniques that may be employed to facilitate communication between device 110 and another computing device include RF communication according to the 802.11 or Bluetooth® specification sets, infrared communication, e.g., according to the IrDA standard, or other standard or proprietary telemetry protocols. In this manner, other external devices may be capable of communicating with device 110 without needing to establish a secure wireless connection.

Power source 118 is configured to deliver operating power to the components of device 110. Power source 118 may include a battery and a power generation circuit to produce the operating power. In some embodiments, the battery may be rechargeable to allow extended operation. Recharging may be accomplished by electrically coupling power source 118 to a cradle or plug that is connected to an alternating current (AC) outlet. Additionally, or alternatively, recharging may be accomplished through proximal inductive interaction between an external charger and an inductive charging coil within device 110. In other embodiments, traditional batteries (e.g., nickel cadmium or lithium ion batteries) may be used. In addition, device 110 may be directly coupled to an alternating current outlet to power device 110. Power source 118 may include circuitry to monitor power remaining within a battery. In this manner, user interface 112 may provide a current battery level indicator or low battery level indicator when the battery needs to be replaced or recharged. In some cases, power source 118 may be capable of estimating the remaining time of operation using the current battery.

The architecture of sensor 100 illustrated in FIG. 10 and device 110 illustrated in FIG. 11 is merely one example and sensor 100 and device 110 should not be limited to the illustrated architectures. In other examples, sensor 100 and/or device 110 may be configured in a variety of other ways. For example, although processing circuitry 106 and telemetry module 104 are described as separate modules, in some examples, processing circuitry 106 and telemetry module 104 may be functionally integrated. In some examples, processing circuitry 106 and telemetry module 104 may correspond to individual hardware units, such as ASICs, DSPs, FPGAs, or other hardware units. Further, although not shown in FIG. 10, sensor 100 may include a memory, such as a memory like memory 116 of device 110.

Figure 12:
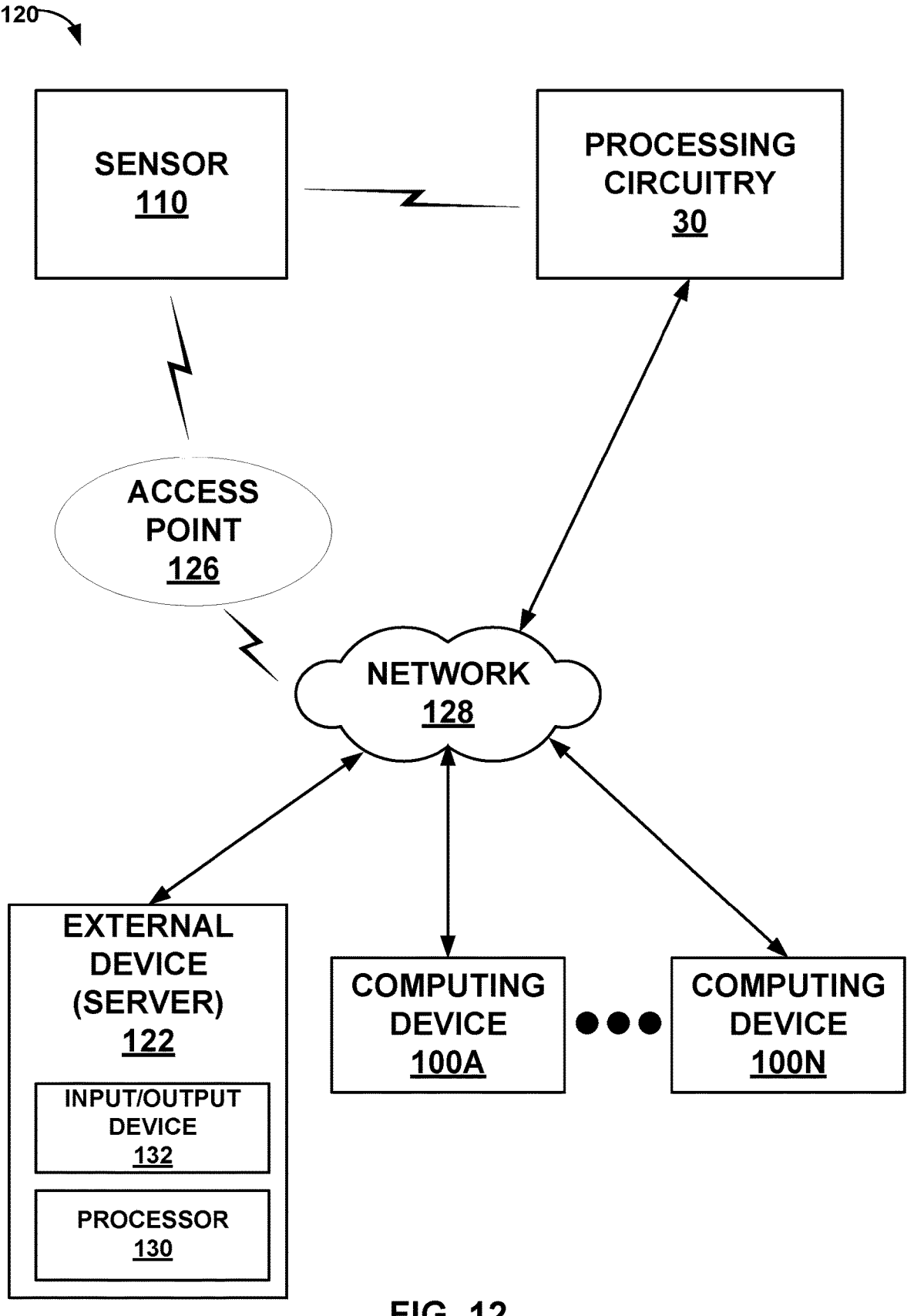
FIG. 12 is a block diagram illustrating an example system that includes an external device, such as a server, and one or more computing devices that are coupled to a sensor and a processing module via a network.

As discussed above, in some examples, sensor 100 may be remotely located from processing circuitry 30 (and device 110). In these examples, sensor 100 may transmit sensed signals or other data generated based on the signals to processing circuitry 30 via any suitable communication. FIG. 12 is a block diagram illustrating an example communication system 120 that can be used. System 120 includes an external device 122, such as a server, and one or more computing devices 124A-124N that are coupled to sensor 100 and processing circuitry 30 via a network 128, according to one example. In this example, sensor 100 uses its telemetry module 104 (FIG. 10) to communicate with processing circuitry 30 via a first wireless connection, and to communicate with an access point 126 via a second wireless connection. In the example of FIG. 7, access point 126, processing circuitry 30, external device 122, and computing devices 124A-124N are interconnected, and able to communicate with each other, through network 128. In some cases, one or more of access point 126, processing circuitry 30, external device 122, and computing devices 124A-124N may be coupled to network 128 through one or more wireless connections. Sensor 100, processing circuitry 30, external device 122, and computing devices 124A-124N may each include one or more processors or processing circuitry, such as one or more microprocessors, DSPs, ASICs, FPGAs, programmable logic circuitry, or the like, that may perform various functions and operations, such as those described herein.

Access point 126 may include a device that connects to network 128 via any of a variety of connections, such as telephone dial-up, digital subscriber line (DSL), or cable modem connections. In other examples, access point 126 may be coupled to network 128 through different forms of connections, including wired or wireless connections. In some examples, access point 126 may communicate with processing circuitry 30 and/or sensor 100. Access point 126 may be co-located with patient 12 (e.g., within the same room or within the same site as patient 12) or may be remotely located from patient 12. For example, access point 126 may be a home monitor that is located in the patient's home or is portable for carrying with patient 12.

During operation, sensor 100 may generate one or more signals indicative of one or more parameters of PD treatment or patient 12. Sensor 100 sends the generated signal to processing circuitry 30, access point 126, and/or external device 122, either wirelessly or via access point 126 and network 128, for remote processing and analysis. For example, sensor 100 may send processing circuitry 30 a signal indicative of a pressure in lumen 22 of catheter 14 (FIG. 1) or external to lumen 22, or a signal indicative of an impedance of a fluid external to catheter 14. Processing circuitry 30 may compare a characteristic, such as an amplitude, of the signal to a predetermined threshold value, determine a trend in the characteristic of the signal, or both. Additionally, or alternatively, processing circuitry 30 may determine a value based on the signal. Then, processing circuitry 30 may generate reports or alerts after analyzing the data, such as by comparing the characteristic to a predetermined threshold value, determining a trend in the characteristic, determining a value, or combinations thereof. In all examples described herein, communication of a signal may refer to the raw signal generate by sensor 100 or other data generated based on the raw signal.

In another example, sensor 100 may provide external device 122 with the generated signal via access point 126 and network 128. External device 122 includes processing circuitry 130. In some cases, external device 122 may request such data, and in some cases, sensor 100 may automatically or periodically provide such data to external device 122. Upon receipt of the signal via input/output device 132, external device 122 can analyze the data and generating reports or alerts upon determination of a particular catheter patency status or peritoneal cavity 16 status. For example, external device 122 may compare a characteristic of the parameter indicated by the signal to detect a catheter blockage, and may present a notification to a user via input/output device 132 indicating the catheter blockage.

In one example, external device 122 may include a secure storage site for information that has been collected from sensor 100 and/or processing circuitry 30. In this example, network 128 may include an Internet network, and trained professionals, such as clinicians, may use computing devices 124A-124N to securely access stored data on external device 122. For example, the trained professionals may need to enter usernames and passwords to access the stored information on external device 122. In one example, external device 122 may be a CareLink server available from Medtronic, Inc., of Minneapolis, MN.

As discussed above, in some examples, processing circuitry 30 is configured to determine one or more parameters related to PD treatment delivered by PD system 10 based on signals generated by sensors 20A, 20B of catheter 14, or any of the other example sensors described herein. A parameter related to PD treatment can include, for example, a catheter patency status or a peritoneal cavity status of the patient.

FIG. 13 is a flow diagram of an example technique for determining a parameter related to PD treatment based on a signal generated by a sensor of a catheter of a PD system. The example technique of FIG. 13, as well as FIGS. 14 and 15, will be described with respect to PD system 10 of FIG. 1. In other examples, however, the example technique of FIG. 13 may be performed by a PD system including another catheter including a pressure sensor and/or an impedance sensor including catheter 50 of FIGS. 4-6 or catheter 80 of FIGS. 7-9. In addition, although processing circuitry 30 is primarily referred to throughout the description of FIGS. 13-15, in other examples, the techniques described with reference to FIGS. 13-15 may be performed by processing circuitry of another device, alone or in combination with processing circuitry 30.

In the technique shown in FIG. 13, processing circuitry 30 receives a pressure signal from pressure sensor 20A and indicative of a pressure in lumen 22 of catheter 14 and/or an impedance signal from impedance sensor 20B and indicative of an impedance of a fluid in lumen 22 (140). As discussed above, processing circuitry 30 can receive the pressure signal and/or the impedance signal from sensors 20A, 20B, respectively, via wired connection or a wireless communication. Processing circuitry 30 compares a characteristic of the pressure signal and/or a characteristic of the impedance signal to a predetermined threshold value (142), which can be stored in memory 78 of device (FIG. 11) or a memory of another device. Processing circuitry 30 may use any suitable characteristic of the signals generated by sensors 20A, 20B to compare to the predetermined threshold value. In some examples, the characteristic of the pressure signal is an absolute value of a sensed pressure in lumen 22 and the characteristic of the impedance signal is an absolute value of an impedance of a fluid in lumen 22.

Processing circuitry 30 determines a status of catheter 14 based on at least one of the comparison of the characteristic to the predetermined threshold value (144). In some examples, the status of catheter 14 is an impairment of catheter 14, e.g., a blockage of catheter 14, a kink in catheter 14, tissue in-growth around an opening of catheter 14, a shift in the position of catheter 14 that blocks a catheter opening, or the like that can result in the reduction of fluid flow rate through lumen 22 of catheter 14. In some examples, processing circuitry 30 determines a catheter status indicating catheter 14 is impaired (e.g., inner lumen 22 is obstructed or an opening of catheter 14 is obstructed) in response to determining the characteristic of the pressure signal is greater than or equal to a predetermined threshold pressure value.

In addition to or instead of detecting the catheter status indicating catheter 14 is impaired based on the pressure signal, in some examples, processing circuitry 30 determines that catheter 14 is impaired in response to determining an impedance of an electrical path in inner lumen 22 of catheter 14 is greater than or equal to a predetermined threshold impedance value. The impedance of an electrical path in inner lumen 22 catheter than or equal to the predetermined impedance value can indicate, for example, that there is a kink or other obstruction proximal to the location of sensor 20 that is limiting or even preventing fluid from flowing from PD cycler 18 to the location of sensor 20B.

In response to determining the catheter indicates catheter 14 is impaired, processing circuitry 30 may generate a notification that notifies a clinician or patient 12 that processing circuitry 30 has detected the adverse catheter status. The notification, as well as other notifications described herein, can be delivered to the patient or the clinician via any suitable user interface, such as via user interface 112 (FIG. 11) of a device that includes processing circuitry 30, via a light or other visible indication on catheter 14 or PD cycler 18, or the like. The notification can include a visible, audible, and/or somatosensory notification.

In addition to or instead of the notification, in some examples, response to determining the catheter indicates catheter 14 is impaired, processing circuitry 30 controls PD cycler 18 to provide a fluid bolus through inner lumen 22 of catheter 14 in an attempt to mitigate the catheter impairment, for example, in an attempt to pulse and/or move catheter 14 within peritoneal cavity 16 and/or dislodge the obstruction of catheter 14.

FIG. 14 is a flow diagram of another example technique for determining a parameter related to PD treatment based on a signal generated by a sensor of a catheter of a PD system. In the technique of FIG. 14, processing circuitry 30 receives a pressure signal from pressure sensor 20A and indicative of a pressure in lumen 22 of catheter 14 and/or an impedance signal from impedance sensor 20B and indicative of an impedance of a fluid in lumen 22 (140). Processing circuitry 30 determines a trend in a characteristic of the pressure signal over time (150), and determines a catheter patency status based on the determined trend (152). Processing circuitry 30 may use any suitable characteristic of the signal generated by sensor 20 to determine the trend.

In some examples, processing circuitry 30 determines a catheter patency status indicating catheter 14 is impaired (e.g., inner lumen 22 is obstructed or an opening of catheter 14 is obstructed) in response to determining the trend indicates a pressure in lumen 22 of catheter 14 has increased over time, e.g., by greater than or equal to a threshold rate of change. For example, processing circuitry 30 may determine that the status of catheter 14 is impaired if the pressure of the fluid in inner lumen 22 has increased by about 1.25 times for a given flow rate indicated by PD cycler 18.

Figure 15:
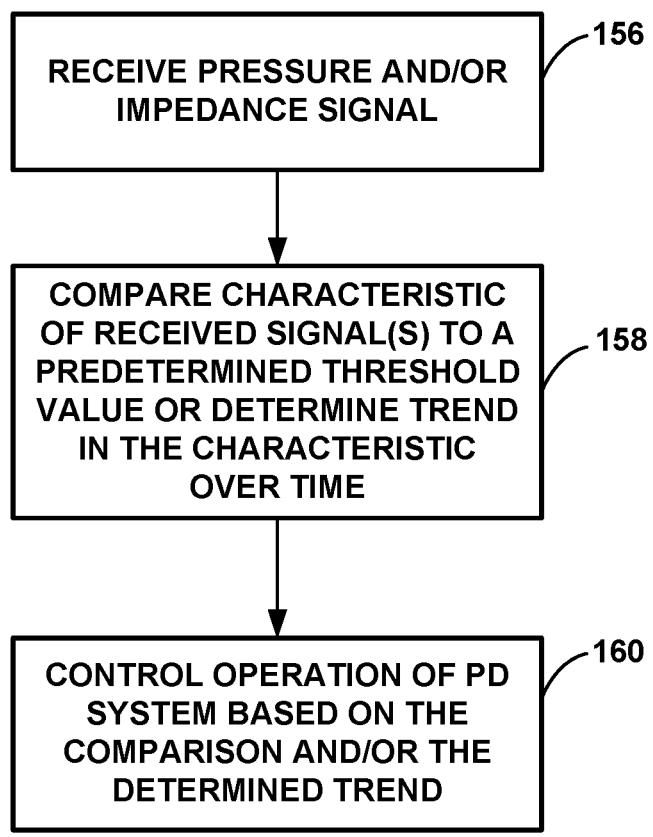

FIG. 15 is flow diagram of another example technique for determining a parameter related to PD treatment based on a signal generated by a sensor of a catheter of a PD system. In the example shown in FIG. 15, the parameter is a status of peritoneal cavity 16 (FIG. 1) of patient 12. In the technique shown in FIG. 15, processing circuitry 30 receives a pressure signal from pressure sensor 20A and indicative of a pressure internal to lumen 22 or external to lumen 22 of catheter 14 and within peritoneal cavity 16 and/or an impedance signal from impedance sensor 20B and indicative of an impedance of a fluid in peritoneal cavity 16 and in contact with impedance sensor 20B (156).

Processing circuitry 30 compares a characteristic of the pressure signal and/or a characteristic of the impedance signal to a predetermined threshold value (158), which can be stored in memory 78 of device (FIG. 11) or a memory of another device. In addition, or instead, processing circuitry 30 determines a trend in the characteristic over time (158). Processing circuitry 30 may use any suitable characteristic of the signals generated by sensor 20A, 20B to compare to the predetermined threshold value or to determine the trend. In some examples, the characteristic of the pressure signal is an absolute value of a pressure in lumen 22 or in peritoneal cavity 16 and the characteristic of the impedance signal is an absolute value of an impedance of a fluid in peritoneal cavity 16 and in contact with impedance sensor 20B.

Processing circuitry 30 controls the operation of PD system 10 based on the comparison and/or based on the determined trend (160). In some examples, a sudden drop in pressure inside lumen 22 of catheter 14 indicated by the signal generated by sensor 20A could indicate enough of the dialysate in peritoneal cavity 16 has been removed. Similarly, a sudden increase in a sensed impedance in peritoneal cavity 16 could indicate enough of the dialysate in peritoneal cavity 16 has been removed. Thus, in some examples, in response to determining the characteristic of the pressure signal indicative of the pressure in lumen 22 of catheter 14 is less than or equal to a predetermined threshold pressure value, determining a rate of decrease in pressure in peritoneal cavity 16 greater than or equal to a predetermined threshold pressure rate of change value, and/or determining a rate of increase of impedance in peritoneal cavity 16 greater than or equal to a predetermined threshold impedance rate of change, processing circuitry 30 can directly or indirectly control PD cycler 18 to reduce the amount of fluid PD cycler 18 removes from peritoneal cavity 16 (e.g., stopping the removal of fluid or significantly decreasing the amount of fluid removed).

In some examples, processing circuitry 30 controls the operation of PD system 10 (160) by at least modifying a prescription for PD treatment provided by PD cycler 18. For example, processing circuitry 30 can determine that there is fluid build-up in peritoneal cavity 16 in response to determining a pressure in peritoneal cavity 16 greater than or equal to a predetermined threshold pressure value and/or a change in pressure in peritoneal cavity 16 over time in greater than or equal to a first predetermined rate of change, and by detecting an impedance in peritoneal cavity 16 is less than or equal to a predetermined threshold impedance value and/or a change impedance in peritoneal cavity 16 over time in greater than or equal to a second predetermined rate of change.

In response to determining that there is fluid build-up in peritoneal cavity 16, controls the operation of PD system 10 (160) by at least modifying an ultrafiltration volume used by PD cycler 18 during the current PD treatment session, if applicable, or during a future PD treatment session. As discussed above, adjusting the ultrafiltration volume impacts the amount of effluent fluid PD cycler 18 removes from peritoneal cavity 16 during the treatment cycle. For example, a higher volume of ultrafiltration results in more effluent fluid being removed from peritoneal cavity 16. Thus, in some examples, in response to determining that there is fluid build-up in peritoneal cavity 16 based on the pressure and impedance signals generated by sensors 20A, 20B, processing circuitry 30 controls PD cycler 18 to increase the ultrafiltration volume during a current or a next PD treatment session in order to remove more fluid from peritoneal cavity 16.

In some examples, processing circuitry 30 controls the operation of PD system 10 (160) based on an impedance signal from impedance sensor 20B and not based on a pressure signal from pressure sensor 20. For example, processing circuitry 30 may determine that a PD prescription, e.g., the concentration of osmotic agent in a dialysate, a dwell period, or a frequency of PD treatment sessions, should be modified in response to determining the characteristic of the impedance signal and indicative of electrical conductivity of fluid in peritoneal cavity 16 is less than or equal to a predetermined threshold impedance value or has decreased over time by greater than or equal to a threshold amount. In some examples, the electrical conductivity being less than or equal to a predetermined threshold value or decreasing over time by greater than or equal to a threshold amount may be indicative of sodium sieving, which in some cases, may be relating to inadequate PD treatment due to an insufficient amount (e.g. concentration) of osmotic agent, too much osmotic agent in a dialysate, an insufficient amount of effluent fluid being removed from peritoneal cavity 16 by PD cycler 18 during a PD treatment cycle, too much effluent fluid being removed from peritoneal cavity 16 by PD cycler 18 during a PD treatment cycle, or the like.

Thus, in some examples, processing circuitry 30 controls the operation of PD system 10 (160) by at least adjusting one or more parameters of the PD cycler 18 in response to determining that a PD prescription should be modified based on the impedance signal. For example, if processing circuitry 30 determines that the impedance of system 10 and indicative of a characteristic (e.g., volume and/or electrical conductivity) of fluid within peritoneal cavity 16 is less than or equal to predetermined threshold impedance value or is decreasing over time by greater than or equal a threshold amount, then processing circuitry 30, alone or with the aid of a clinician, may adjust the dwell period, dialysate type, or osmotic agent concentration, number of PD treatment cycles per unit time, or other parameters relating to the PD treatment for patient 12.

The techniques described in this disclosure, including those attributed to sensor 20, processing circuitry 30, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computerreadable medium such as RAM, ROM, NVRAM, EEPROM, FLASH memory, magnetic data storage media, optical data storage media, or the like. The instructions may be executed to support one or more aspects of the functionality described in this disclosure.

This disclosure includes the following non-limiting examples.

Example 1: A catheter includes an elongated catheter body defining a lumen; and a plurality of sensors includes a pressure sensor configured to generate a pressure signal indicative of a pressure of fluid within the lumen or external to the lumen; and an impedance sensor configured to generate an impedance signal indicative of an impedance of an electrical path within the lumen or external to the lumen.

Example 2: The catheter of example 1, wherein at least some sensors of the plurality of sensors are positioned along an inner surface of the catheter body, the catheter further comprising an inner cover positioned along the inner surface, the inner cover defining openings aligned with the at least some sensors of the plurality of sensors.

Example 3: The catheter of example 2, further comprising at least one electrical conductor configured to electrically connect at least one of the pressure sensor or the impedance sensor to processing circuitry, wherein the at least one electrical conductor is positioned between the inner cover and the catheter body.

Example 4: The catheter of example 3, wherein the inner surface of the catheter body defines a channel and the at least one electrical conductor and the at least one of the pressure sensor or the impedance sensor are positioned within the channel.

Example 5: The catheter of any of examples 1-4, wherein at least some sensors of the plurality of sensors are positioned on an outer surface of the catheter body, the catheter further comprising an outer cover defining openings aligned with the at least some sensors of the plurality of sensors.

Example 6: The catheter of example 5, further comprising at least one electrical conductor configured to electrically connect at least one of the pressure sensor or the impedance sensor to processing circuitry, wherein the at least one electrical conductor is positioned between the outer cover and the catheter body.

Example 7: The catheter of example 6, wherein the catheter body defines a channel and the at least one electrical conductor and the at least one of the pressure sensor or the impedance sensor are positioned within the channel.

Example 8: The catheter of any of examples 4-7, wherein the at least one of the pressure sensor or the impedance sensor is fully recessed in the channel.

Example 9: The catheter of any of examples 4-7, wherein the at least one of the pressure sensor or the impedance sensor is partially recessed in the channel.

Example 10: The catheter of any of examples 4 or 7-9, wherein the channel is a first channel, the catheter body further defining a second channel, wherein the pressure sensor is positioned in the first channel and the impedance sensor is positioned in the second channel.

Example 11: The catheter of any of examples 1-9, wherein at least one of the pressure sensor or the impedance sensor is configured to wirelessly transmit the respective pressure signal or impedance signal to processing circuitry.

Example 12: A system includes the catheter of any of examples 1-11; and processing circuitry configured to: receive the pressure signal and the impedance signal; and determine a parameter related to peritoneal dialysis treatment based on at least one of the pressure signal or the impedance signal.

Example 13: The system of example 12, wherein the pressure signal is indicative of pressure of fluid within the lumen, and wherein the processing circuitry is configured to determine the parameter related to peritoneal dialysis treatment by at least: comparing a characteristic of the pressure signal to a predetermined threshold pressure value; and determining a status of the catheter based on the comparison.

Example 14: The system of example 13, wherein the processing circuitry is configured to compare the characteristic of the pressure signal to the predetermined threshold pressure value by at least determining whether the characteristic is greater than or less than the predetermined threshold pressure value, and determine the status of the catheter by at least detecting a blockage of the catheter in response to determining the characteristic is greater than or less than the predetermined threshold pressure value.

Example 15: The system of any of examples 12-14, wherein the impedance signal is indicative of impedance of an electrical path within the lumen, and wherein the processing circuitry is configured to determine the parameter related to peritoneal dialysis treatment by at least: comparing a characteristic of the impedance signal to a predetermined threshold impedance value; and determining a status of the catheter based on the comparison.

Example 16: The system of example 15, wherein the processing circuitry is configured to compare the characteristic of the impedance signal to the predetermined threshold impedance value by at least determining whether the characteristic is less than or equal to the predetermined threshold impedance value and determine the status of the catheter by at least detecting a blockage of the catheter in response to determining the characteristic is less than or equal to the predetermined threshold impedance value.

Example 17: The system of any of examples 13-16, wherein the status of the catheter comprises an impairment that reduces a fluid flow rate through the lumen.

Example 18: The system of example 17, wherein the impairment comprises at least one of a blockage of the lumen of the catheter, a blockage of an opening to the lumen of the catheter, or a kink in the catheter.

Example 19: The system of any of examples 13-18, wherein the processing circuitry is further configured to control a peritoneal dialysis cycler based on the catheter status.

Example 20: The system of example 19, wherein the processing circuitry is configured to control the peritoneal dialysis cycler based on the catheter status by at least controlling the peritoneal dialysis cycler to deliver a bolus of fluid through the lumen of the catheter.

Example 21: The system of any of examples 13-20, further comprising a user interface, wherein the processing circuitry is further configured to present a notification via the user interface based on the catheter status.

Example 22: The system of any of examples 12-21, wherein the pressure signal is indicative of pressure of fluid within the lumen, and wherein the processing circuitry is configured to: determine a trend in a characteristic of the pressure signal over time; and determine a status of the catheter based on the determined trend.

Example 23: The system of example 22, wherein the status of the catheter comprises an impairment that reduces a fluid flow rate through the lumen, and wherein the processing circuitry is configured to detect the impairment in response to determining the trend indicates the pressure is increasing over time.

Example 24: The system of example 23, wherein the impairment comprises at least one of a blockage of the lumen of the catheter, a blockage of an opening to the lumen of the catheter, or a kink in the catheter.

Example 25: The system of any of examples 23 and 24 or any of examples 23 and 24, wherein the processing circuitry is further configured to control a peritoneal dialysis cycler in response to detecting the impairment of the catheter.

Example 26: The system of example 25, wherein the processing circuitry is configured to control the peritoneal dialysis cycler by at least controlling the peritoneal dialysis cycler to deliver a bolus of fluid through the lumen of the catheter in response to detecting the impairment of the catheter.

Example 27: The system of any of examples 23-26, further comprising a user interface, wherein the processing circuitry is further configured to present a notification via the user interface in response to detecting the impairment of the catheter.

Example 28: The system of any of examples 12 through 27, wherein the pressure signal is indicative of pressure of fluid internal to the lumen, and wherein the processing circuitry is configured to: compare a characteristic of the pressure signal to a predetermined threshold pressure value; and control an operation of a peritoneal dialysis cycler based on the comparison.

Example 29: The system of example 28, wherein the processing circuitry is configured to compare the characteristic of the pressure signal to the predetermined threshold pressure value by at least determining the characteristic is less than or equal to the predetermined threshold pressure value, and wherein the processing circuitry is configured control the operation of the peritoneal dialysis cycler by least controlling the peritoneal dialysis cycler to decrease an amount of fluid the peritoneal dialysis cycler removes from the peritoneal cavity in response to determining the characteristic is less than or equal to the predetermined threshold pressure value.

Example 30: The system of any of examples 12 through 29, wherein the pressure signal is indicative of pressure of fluid external to the lumen, and wherein the processing circuitry is configured to: determine a rate of change of a characteristic of the pressure signal over time; and control an operation of a peritoneal dialysis cycler based on the determined rate of change.

Example 31: The system of example 30, wherein the processing circuitry is configured to determine the rate of change indicates the pressure is decreasing by greater than or equal to a predetermined threshold rate of change value, and to control the operation of the peritoneal dialysis cycler by at least controlling the peritoneal dialysis cycler to decrease an amount of fluid the peritoneal dialysis cycler removes from the peritoneal cavity in response to determining the rate of change indicates the pressure is decreasing by greater than or equal to a predetermined threshold rate of change value.

Example 32: The system of any of examples 12 or 28-31, wherein the impedance signal is indicative of impedance of fluid external to the lumen, and wherein the processing circuitry is configured to: determine a rate of change of a characteristic of the impedance signal over time; and control an operation of a peritoneal dialysis cycler based on the determined rate of change.

Example 33: The system of example 32, wherein the processing circuitry is configured to determine the rate of change indicates the impedance is increasing by greater than or equal to a predetermined threshold rate of change value, and to control the operation of the peritoneal dialysis cycler by at least controlling the peritoneal dialysis cycler to decrease an amount of fluid the peritoneal dialysis cycler removes from the peritoneal cavity in response to determining the rate of change indicates the impedance is increasing by greater than or equal to a predetermined threshold rate of change value.

Example 34: The system of any of examples 12-33, wherein the pressure signal is indicative of pressure external to the lumen and the impedance signal is indicative of pressure external to the lumen, and wherein the processing circuitry is configured to: at least one of compare a characteristic of the pressure signal to a predetermined threshold pressure value or determine a first rate of change of the characteristic of the pressure signal over time; at least one of compare a characteristic of the impedance signal to a predetermined threshold impedance value or determine a second rate of change of the characteristic of the impedance signal over time; and control an operation of a peritoneal dialysis cycler based on at least one of the comparison of the characteristic of the pressure signal to the predetermined threshold pressure value or the first rate of change, and based on at least one of the comparison of the characteristic of the impedance signal to the predetermined threshold impedance value or the second rate of change.

Example 35: The system of example 34, wherein the processing circuitry is configured to control the operation of the peritoneal dialysis cycler by at least modifying an ultrafiltration volume used by the peritoneal dialysis cycler in response to determining: at least one of: the characteristic of the pressure signal is greater than or equal to the predetermined threshold pressure value; or the first rate of change is greater than or equal to a first predetermined rate of change; and at least one of: the characteristic of the impedance signal is less than or equal to the predetermined impedance value; or the second rate of change is greater than or equal to a second predetermined rate of change.

Example 36: The system of example 34 or example 35, wherein the processing circuitry is configured to control the operation of the peritoneal dialysis cycler by at least modifying a concentration of an osmotic agent in a dialysate delivered to the peritoneal cavity by the peritoneal dialysis cycler in response to determining: at least one of: the characteristic of the pressure signal is greater than or equal to the predetermined threshold pressure value; or the first rate of change is greater than or equal to a first predetermined rate of change; and at least one of: the characteristic of the impedance signal is less than or equal to the predetermined impedance value; or the second rate of change is greater than or equal to a second predetermined rate of change.

Example 37: The system of any of examples 34-36, wherein the processing circuitry is configured to control the operation of a peritoneal dialysis cycler by at least modifying a dwell period applied by the peritoneal dialysis cycler in response to determining: at least one of: the characteristic of the pressure signal is greater than or equal to the predetermined threshold pressure value; or the first rate of change is greater than or equal to a first predetermined rate of change; and at least one of: the characteristic of the impedance signal is less than or equal to the predetermined impedance value; or the second rate of change is greater than or equal to a second predetermined rate of change.

Example 38: A catheter includes an elongated catheter body defining a lumen and a channel; a pressure sensor configured to generate a pressure signal indicative of a pressure of fluid within the lumen or external to the lumen; an impedance sensor configured to generate an impedance signal indicative of a characteristic of fluid within the lumen or external to the lumen; and a cover at least partially covering the channel, wherein at least one of the pressure sensor or the impedance sensor are positioned in the channel, the cover defining an opening aligned with the at least one of the pressure sensor or the impedance sensor.

Example 39: The catheter of example 38, wherein an inner surface of the catheter body defines the channel and the cover is radially inward of the catheter body.

Example 40: The catheter of any of examples 38 and 39, wherein an outer surface of the catheter body defines the channel and the cover is radially outward of the catheter body.

Example 41: The catheter of any of examples 38-40, further comprising an electrical conductor configured to electrically connect the at least one of the pressure sensor or the impedance sensor to processing circuitry, wherein the electrical conductor is in the channel and covered by the cover.

Example 42: A method includes introducing a catheter of any of examples 1-11 or 38-41 into a peritoneal cavity of a patient of a patient.

Example 43: A method includes receiving, by processing circuitry, a pressure signal from a pressure sensor indicative of a pressure of fluid within a lumen defined by an elongated catheter body of a catheter or external to the lumen; receiving, by the processing circuitry, an impedance signal indicative of an impedance of an electrical path within the lumen or external to the lumen; and determining a parameter related to peritoneal dialysis treatment based on at least one of the pressure signal or the impedance signal.

Example 44: The method of example 43, wherein at least one of the pressure sensor or the impedance sensor are positioned along an inner surface of the catheter body, the catheter further comprising an inner cover positioned along the inner surface, the inner cover defining openings aligned with the at least one of the pressure sensor or the impedance sensor.

Example 45: The method of example 44, wherein the catheter further comprises at least one electrical conductor configured to electrically connect at least one of the pressure sensor or the impedance sensor to the processing circuitry, wherein the at least one electrical conductor is positioned between the inner cover and the catheter body.

Example 46: The method of example 45, wherein the inner surface of the catheter body defines a channel and the at least one electrical conductor and the at least one of the pressure sensor or the impedance sensor are positioned within the channel.

Example 47: The method of any of examples 43-46, wherein at least one of the pressure sensor or the impedance sensor are positioned an outer surface of the catheter body, the catheter further comprising an outer cover defining openings aligned with the at least some of the plurality of sensors.

Example 48: The method of example 47, wherein the catheter further comprises at least one electrical conductor configured to electrically connect at least one of the pressure sensor or the impedance sensor to the processing circuitry, wherein the at least one electrical conductor is positioned between the outer cover and the catheter body.

Example 49: The method of example 48, wherein the catheter body defines a channel and the at least one electrical conductor and the at least one of the pressure sensor or the impedance sensor are positioned within the channel.

Example 50: The method of example 46 or example 49, wherein the at least one of the pressure sensor or the impedance sensor is fully recessed in the channel.

Example 51: The method of example 46 or example 49, wherein the at least one of the pressure sensor or the impedance sensor is partially recessed in the channel.

Example 52: The method of any of examples 46-51, wherein the channel is a first channel, the catheter body further defining a second channel, wherein the pressure sensor is positioned in the first channel and the impedance sensor is positioned in the second channel.

Example 53: The method of any of examples 43-52, wherein at least one of the pressure sensor or the impedance sensor is configured to wirelessly transmit the respective pressure signal or impedance signal to processing circuitry.

Example 54: The method of any of examples 43-53, wherein the pressure signal is indicative of pressure of fluid within the lumen, and wherein determining the parameter related to peritoneal dialysis treatment comprises: comparing, by the processing circuitry, a characteristic of the pressure signal to a predetermined threshold pressure value; and determining, by the processing circuitry, a status of the catheter based on the comparison.

Example 55: The method of example 54, wherein comparing the characteristic of the pressure signal to the predetermined threshold pressure value comprises determining whether the characteristic is greater than or less than the predetermined threshold pressure value, and wherein determining the status of the catheter comprises detecting a blockage of the catheter in response to determining the characteristic is greater than or less than the predetermined threshold pressure value.

Example 56: The method of any of examples 43-55, wherein the impedance signal is indicative of impedance of an electrical path within the lumen, and wherein determining the parameter related to peritoneal dialysis treatment comprises: comparing a characteristic of the impedance signal to a predetermined threshold impedance value; and determining a status of the catheter based on the comparison.

Example 57: The method of example 56, wherein comparing the characteristic of the impedance signal to the predetermined threshold impedance value comprises determining whether the characteristic is less than or equal to the predetermined threshold impedance value, and wherein determining the status of the catheter comprises detecting a blockage of the catheter in response to determining the characteristic is less than or equal to the predetermined threshold impedance value.

Example 58: The method of any of examples 54-57, wherein the status of the catheter comprises an impairment that reduces a fluid flow rate through the lumen.

Example 59: The method of example 58, wherein the impairment comprises at least one of a blockage of the lumen of the catheter, a blockage of an opening to the lumen of the catheter, or a kink in the catheter.

Example 60: The method of any of examples 54-59, further comprising controlling a peritoneal dialysis cycler based on the catheter status.

Example 61: The method of example 60, wherein controlling the peritoneal dialysis cycler based on the catheter status comprises controlling the peritoneal dialysis cycler to deliver a bolus of fluid through the lumen of the catheter.

Example 62: The method of any of examples 54-61, further comprising presenting, by the processing circuitry, a notification via a user interface based on the catheter status.

Example 63: The method of any of examples 43-62, wherein the pressure signal is indicative of pressure of fluid within the lumen, the method further includes determining, by the processing circuitry, a trend in a characteristic of the pressure signal over time; and determining, by the processing circuitry, a status of the catheter based on the determined trend.

Example 64: The method of example 63, wherein the status of the catheter comprises an impairment that reduces a fluid flow rate through the lumen, and wherein determining the status of the catheter comprises detecting the impairment in response to determining the trend indicates the pressure is increasing over time.

Example 65: The method of example 64, wherein the impairment comprises at least one of a blockage of the lumen of the catheter, a blockage of an opening to the lumen of the catheter, or a kink in the catheter.

Example 66: The method of any of examples 64 and 65 or any of examples 64 and 65, further comprising controlling a peritoneal dialysis cycler in response to detecting the impairment of the catheter.

Example 67: The method of example 66, wherein controlling the peritoneal dialysis cycler comprises controlling the peritoneal dialysis cycler to deliver a bolus of fluid through the lumen of the catheter in response to detecting the impairment of the catheter.

Example 68: The method of any of examples 64-67, further comprising presenting, via a user interface, a notification via the user interface in response to detecting the impairment of the catheter.

Example 69: The method of any of examples 43 through 68, wherein the pressure signal is indicative of pressure of fluid internal to the lumen, and wherein the method further comprises: comparing, by the processing circuitry, a characteristic of the pressure signal to a predetermined threshold pressure value; and controlling, by the processing circuitry, an operation of a peritoneal dialysis cycler based on the comparison.

Example 70: The method of example 69, wherein comparing the characteristic of the pressure signal to the predetermined threshold pressure value comprises determining the characteristic is less than or equal to the predetermined threshold pressure value, and wherein controlling the operation of the peritoneal dialysis cycler comprises controlling the peritoneal dialysis cycler to decrease an amount of fluid the peritoneal dialysis cycler removes from the peritoneal cavity in response to determining the characteristic is less than or equal to the predetermined threshold pressure value.

Example 71: The method of any of examples 43 through 70, wherein the pressure signal is indicative of pressure of fluid external to the lumen, and wherein the method further comprises: determining, by the processing circuitry, a rate of change of a characteristic of the pressure signal over time; and controlling, by the processing circuitry, an operation of a peritoneal dialysis cycler based on the determined rate of change.

Example 72: The method of example 71, further comprising determining, by the processing circuitry, the rate of change indicates the pressure is decreasing by greater than or equal to a predetermined threshold rate of change value, and wherein controlling the operation of the peritoneal dialysis cycler comprises controlling the peritoneal dialysis cycler to decrease an amount of fluid the peritoneal dialysis cycler removes from the peritoneal cavity in response to determining the rate of change indicates the pressure is decreasing by greater than or equal to a predetermined threshold rate of change value.

Example 73: The method of any of examples 43-72, wherein the impedance signal is indicative of impedance of fluid external to the lumen, and wherein the method further comprises: determining, by the processing circuitry, a rate of change of a characteristic of the impedance signal over time; and controlling, by the processing circuitry, an operation of a peritoneal dialysis cycler based on the determined rate of change.

Example 74: The method of example 73, further comprising determining, by the processing circuitry, the rate of change indicates the impedance is increasing by greater than or equal to a predetermined threshold rate of change value, wherein controlling the operation of the peritoneal dialysis cycler comprises controlling the peritoneal dialysis cycler to decrease an amount of fluid the peritoneal dialysis cycler removes from the peritoneal cavity in response to determining the rate of change indicates the impedance is increasing by greater than or equal to a predetermined threshold rate of change value.

Example 75: The method of any of any of examples 43-70, wherein the pressure signal is indicative of pressure external to the lumen and the impedance signal is indicative of pressure external to the lumen, the method further includes at least one of comparing, by the processing circuitry, a characteristic of the pressure signal to a predetermined threshold pressure value or determining, by the processing circuitry, a first rate of change of the characteristic of the pressure signal over time; at least one of comparing, by the processing circuitry, a characteristic of the impedance signal to a predetermined threshold impedance value or determining, by the processing circuitry, a second rate of change of the characteristic of the impedance signal over time; and controlling, by the processing circuitry, an operation of a peritoneal dialysis cycler based on at least one of the comparison of the characteristic of the pressure signal to the predetermined threshold pressure value or the first rate of change, and based on at least one of the comparison of the characteristic of the impedance signal to the predetermined threshold impedance value or the second rate of change.

Example 76: The method of example 75, wherein controlling the operation of the peritoneal dialysis cycler comprises modifying an ultrafiltration volume used by the peritoneal dialysis cycler in response to determining: at least one of: the characteristic of the pressure signal is greater than or equal to the predetermined threshold pressure value; or the first rate of change is greater than or equal to a first predetermined rate of change; and at least one of: the characteristic of the impedance signal is less than or equal to the predetermined impedance value; or the second rate of change is greater than or equal to a second predetermined rate of change.

Example 77: The method of any of examples 75 or example 76, wherein controlling the operation of the peritoneal dialysis cycler by at least modifying a concentration of an osmotic agent in a dialysate delivered to the peritoneal cavity by the peritoneal dialysis cycler in response to determining: at least one of: the characteristic of the pressure signal is greater than or equal to the predetermined threshold pressure value; or the first rate of change is greater than or equal to a first predetermined rate of change; and at least one of: the characteristic of the impedance signal is less than or equal to the predetermined impedance value; or the second rate of change is greater than or equal to a second predetermined rate of change.

Example 78: The method of any of examples 75-77, wherein controlling the operation of the peritoneal dialysis cycler comprises modifying a dwell period applied by the peritoneal dialysis cycler in response to determining: at least one of: the characteristic of the pressure signal is greater than or equal to the predetermined threshold pressure value;

or the first rate of change is greater than or equal to a first predetermined rate of change; and at least one of: the characteristic of the impedance signal is less than or equal to the predetermined impedance value; or the second rate of change is greater than or equal to a second predetermined rate of change.

Various examples have been described. These and other examples are within the scope of the following claims.

What is claimed is:

1. A system, comprising:

a catheter comprising:

an elongated catheter body defining a lumen and a longitudinal axis;

a channel extending parallel to the longitudinal axis and formed in a portion of an outer wall of the elongated catheter body, wherein at least a portion of the elongated catheter body is disposed between the lumen and the channel; and a plurality of sensors comprising:

a pressure sensor configured to generate a pressure signal indicative of a pressure of fluid within the lumen or external to the lumen, and an impedance sensor disposed on or in the catheter and configured to generate an impedance signal indicative of an impedance of an electrical path within the lumen or external to the lumen, wherein, when the impedance sensor generates the impedance signal, the impedance sensor is disposed within a patient, wherein at least one of the plurality of sensors is disposed within the channel;

an outer cover configured to partially cover the channel and the elongated catheter body, wherein the outer cover includes at least one opening aligned with the at least one of the plurality of sensors disposed within the channel;

wherein the at least one of the plurality of sensors disposed within the channel is positioned such that the at least one of the plurality of sensors extends beyond an outermost surface of the outer cover;

and processing circuitry configured to:

receive the pressure signal and the electrical impedance signal;

adjust a sampling frequency, based on a duration of therapy administered to the patient, of at least one of the plurality of sensors;

determine a first parameter related to peritoneal dialysis treatment based on the pressure signal and the electrical impedance signal, wherein the first parameter includes a volume of the fluid within a peritoneal cavity; and determine a second parameter related to the peritoneal dialysis treatment based on the electrical impedance signal, wherein the second parameter is indicative of a need to remove additional effluent fluid from the peritoneal cavity.

2. The system of claim 1, wherein the pressure signal is indicative of pressure of fluid within the lumen, and wherein the processing circuitry is configured to determine the parameter related to peritoneal dialysis treatment by at least:

comparing a characteristic of the pressure signal to a predetermined threshold pressure value; and determining a status of the catheter based on the comparison.

3. The system of claim 2, wherein the processing circuitry is configured to compare the characteristic of the pressure signal to the predetermined threshold pressure value by at least determining whether the characteristic is greater than or less than the predetermined threshold pressure value, and determine the status of the catheter by at least detecting a blockage of the catheter based on whether the characteristic is greater than or less than the predetermined threshold pressure value.

4. The system of claim 2, wherein the status of the catheter comprises an impairment that reduces a fluid flow rate through the lumen.

5. The system of claim 2, wherein the processing circuitry is further configured to control a peritoneal dialysis cycler based on the status of the catheter.

6. The system of claim 5, wherein the processing circuitry is configured to control the peritoneal dialysis cycler based on the status of the catheter by at least controlling the peritoneal dialysis cycler to deliver a bolus of fluid through the lumen of the catheter.

7. The system of claim 2, further comprising a user interface, wherein the processing circuitry is further configured to present a notification via the user interface based on the status of the catheter.

8. The system of claim 1, wherein the pressure signal is indicative of pressure of fluid within the lumen, and wherein the processing circuitry is configured to:

determine a trend in a characteristic of the pressure signal over time; and determine a status of the catheter based on the determined trend.

9. The system of claim 8, wherein the status of the catheter comprises an impairment that reduces a fluid flow rate through the lumen, and wherein the processing circuitry is configured to detect the impairment in response to determining the trend indicates the pressure is increasing over time.

10. The system of claim 9, wherein the processing circuitry is further configured to control a peritoneal dialysis cycler in response to detecting the impairment of the catheter.

11. The system of claim 9, further comprising a user interface, wherein the processing circuitry is further configured to present a notification via the user interface in response to detecting the impairment of the catheter.

12. The system of claim 1, wherein the pressure signal is indicative of pressure of fluid internal to the lumen, and wherein the processing circuitry is configured to:

at least one of (1) compare a characteristic of the pressure signal to a predetermined threshold pressure value or (2) determine a rate of change of the characteristic of the pressure signal over time; and control an operation of a peritoneal dialysis cycler based on the comparison or the determined rate of change.

13. The system of claim 12, wherein the processing circuitry is configured to compare the characteristic of the pressure signal to the predetermined threshold pressure value by at least determining the characteristic is less than or equal to the predetermined threshold pressure value, and wherein the processing circuitry is configured to control the operation of the peritoneal dialysis cycler by at least controlling the peritoneal dialysis cycler to decrease an amount of fluid the peritoneal dialysis cycler removes from a peritoneal cavity of a patient in response to determining the characteristic is less than or equal to the predetermined threshold pressure value.

14. The system of claim 12, wherein the processing circuitry is configured to determine if the rate of change indicates the pressure is decreasing by greater than or equal to a predetermined threshold rate of change value, and to control the operation of the peritoneal dialysis cycler by at least controlling the peritoneal dialysis cycler to decrease an amount of fluid the peritoneal dialysis cycler removes from a peritoneal cavity of a patient in response to determining the rate of change indicates the pressure is decreasing by greater than or equal to the predetermined threshold rate of change value.

15. The system of claim 1, wherein the pressure signal is indicative of pressure external to the lumen and the electrical impedance signal is indicative of electrical impedance of fluid external to the lumen, and wherein the processing circuitry is configured to:

at least one of compare a characteristic of the pressure signal to a predetermined threshold pressure value or determine a first rate of change of the characteristic of the pressure signal over time;

at least one of compare a characteristic of the electrical impedance signal to a predetermined threshold electrical impedance value or determine a second rate of change of the characteristic of the electrical impedance signal over time; and control an operation of a peritoneal dialysis cycler based on at least one of the comparison of the characteristic of the pressure signal to the predetermined threshold pressure value or the first rate of change, and based on at least one of the comparison of the characteristic of the electrical impedance signal to the predetermined threshold electrical impedance value or the second rate of change.

16. The system of claim 15, wherein the processing circuitry is configured to control the operation of the peritoneal dialysis cycler by at least modifying an ultrafiltration volume used by the peritoneal dialysis cycler in response to determining:

at least one of:

the characteristic of the pressure signal is greater than or equal to the predetermined threshold pressure value; or the first rate of change is greater than or equal to a first predetermined rate of change; and at least one of:

the characteristic of the electrical impedance signal is less than or equal to the predetermined electrical impedance value; or the second rate of change is greater than or equal to a second predetermined rate of change.

17. The system of claim 15, wherein the processing circuitry is configured to control the operation of the peritoneal dialysis cycler by at least modifying a concentration of an osmotic agent in a dialysate delivered to a peritoneal cavity of a patient by the peritoneal dialysis cycler in response to determining:

at least one of:

the characteristic of the pressure signal is greater than or equal to the predetermined threshold pressure value; or the first rate of change is greater than or equal to a first predetermined rate of change; and at least one of:

the characteristic of the electrical impedance signal is less than or equal to the predetermined electrical impedance value; or the second rate of change is greater than or equal to a second predetermined rate of change.

18. The system of claim 15, where in the processing circuitry is configured to control the operation of a peritoneal dialysis cycler by at least modifying a dwell period applied by the peritoneal dialysis cycler in response to determining:

at least one of:

the characteristic of the pressure signal is greater than or equal to the predetermined threshold pressure value; or the first rate of change is greater than or equal to a first predetermined rate of change; and at least one of:

the characteristic of the electrical impedance signal is less than or equal to the predetermined electrical impedance value; or the second rate of change is greater than or equal to a second predetermined rate of change.

19. The system of claim 1, wherein the electrical impedance signal is indicative of impedance of an electrical path within the lumen, and wherein the processing circuitry is configured to determine the parameter related to peritoneal dialysis treatment by at least:

comparing a characteristic of the electrical impedance signal to a predetermined threshold electrical impedance value; and determining a status of the catheter based on the comparison.

20. The system of claim 19, wherein the processing circuitry is configured to compare the characteristic of the electrical impedance signal to the predetermined threshold electrical impedance value by at least determining whether the characteristic is less than or equal to the predetermined threshold electrical impedance value and determine the status of the catheter by at least detecting a blockage of the catheter based on whether the characteristic is less than or equal to the predetermined threshold electrical impedance value.

21. The system of claim 1, wherein the electrical impedance signal is indicative of electrical impedance of fluid external to the lumen, and wherein the processing circuitry is configured to:

determine a rate of change of a characteristic of the electrical impedance signal over time; and control an operation of a peritoneal dialysis cycler based on the determined rate of change.

22. The system of claim 21, wherein the processing circuitry is configured to determine if the rate of change indicates the electrical impedance is increasing by greater than or equal to a predetermined threshold rate of change value, and to control the operation of the peritoneal dialysis cycler by at least controlling the peritoneal dialysis cycler to decrease an amount of fluid the peritoneal dialysis cycler removes from a peritoneal cavity of a patient in response to determining the rate of change indicates the electrical impedance is increasing by greater than or equal to a predetermined threshold rate of change value.

23. The system of claim 1, further comprising at least one electrical conductor configured to electrically connect at least one sensor of the plurality of sensors to processing circuitry, wherein the at least one electrical conductor is positioned between the outer cover and the catheter body.

24. The system of claim 1, wherein at least one of the pressure sensor or the impedance sensor is configured to wirelessly transmit the respective pressure signal or impedance signal to processing circuitry.

25. The system of claim 1, wherein the at least one opening is radially aligned with the at least one of the plurality of sensors disposed within the channel.

26. The system of claim 1, wherein the opening is cutout through the outer cover to expose the at least one of the plurality of sensors disposed within the channel to the fluid within the peritoneal cavity, when the system is disposed within the peritoneal cavity of the patient.

27. The system of claim 1, wherein the channel terminates at a distal end of a distal most sensor of the at least one of the plurality of sensors disposed within the channel.

28. The system of claim 1, wherein the at least one of the plurality of sensors disposed within the channel is positioned such that the at least one of the plurality of sensors extends beyond an outermost surface of the elongated catheter body.

29. A system, comprising:

a catheter comprising:

an elongated catheter body defining a lumen and a channel, a pressure sensor configured to generate a pressure signal indicative of a pressure of fluid within the lumen or external to the lumen, and an impedance sensor configured to generate an electrical impedance signal indicative of a characteristic of fluid within the lumen or external to the lumen; and a cover at least partially covering the channel, wherein at least one of the pressure sensor or the impedance sensor are positioned in the channel, the cover defining an opening aligned with the at least one of the pressure sensor or the impedance sensor;

wherein at least one of the pressure sensor or the impedance sensor is positioned within the channel such that the at least one of the pressure sensor or the impedance sensor extends beyond an outermost surface of the cover; and processing circuitry configured to:

receive the pressure signal and the electrical impedance signal;

determine a parameter related to peritoneal dialysis treatment based on the pressure signal and the electrical impedance signal, wherein the parameter includes at least one of a patient parameter, a parameter indicative of a catheter patency status, a parameter indicative of a peritoneal cavity status, a parameter indicative of a peritoneal hemodynamic status, or a volume of fluid; and control an operation of a peritoneal dialysis cycler based on the parameter.

30. The catheter of claim 29, wherein an outer surface of the catheter body defines the channel and the cover is radially outward of the catheter body.

31. A method comprising:

receiving, by processing circuitry, a pressure signal from a pressure sensor indicative of a pressure of fluid within a lumen defined by an elongated catheter body of a catheter or external to the lumen, receiving, by the processing circuitry, an impedance signal from an impedance sensor indicative of an impedance of an electrical path within the lumen or external to the lumen, wherein the impedance sensor is disposed within a channel extending parallel to a longitudinal axis defined by the elongated catheter body and formed in a portion of an outer wall of the elongated catheter body, wherein at least a portion of the elongated catheter body is disposed between the lumen and the channel, wherein the catheter includes an outer cover configured to partially cover the channel and the elongated catheter body, wherein the outer cover includes an opening aligned with the impedance sensor disposed within the channel;

wherein the impedance sensor disposed within the channel is positioned such that the impedance sensor extends beyond an outermost surface of the outer cover;

adjusting, by the processing circuitry, a sampling frequency of at least one of the pressure signal, the impedance signal, or any combination thereof, based on a duration of a peritoneal dialysis therapy administered to a patient; and determining a parameter related to the peritoneal dialysis treatment based on the pressure signal and the impedance signal.

32. The method of claim 31, wherein determining the parameter related to peritoneal dialysis treatment comprises:

at least one of:

comparing, by the processing circuitry, a characteristic of the pressure signal to a predetermined threshold pressure value, determining a trend in the characteristic of the pressure signal over time, or determining a rate of change of the characteristic of the pressure signal over time; and determining, by the processing circuitry, a status of the catheter based on the comparison, the determined trend, or the determined rate of change.

33. The method of claim 32, further comprising controlling a peritoneal dialysis cycler based on the status of the catheter.

34. The method of claim 31, further comprising:

at least one of:

comparing, by the processing circuitry, a characteristic of the pressure signal to a predetermined threshold pressure value, or determining a rate of change of the characteristic of the pressure signal over time; and controlling, by the processing circuitry, an operation of a peritoneal dialysis cycler based on the comparison or the determined rate of change.

35. The method of claim 31, wherein determining the parameter related to peritoneal dialysis treatment comprises:

at least one of:

comparing a characteristic of the impedance signal to a predetermined threshold impedance value, determining a trend in the characteristic of the impedance signal over time, or determining a rate of change of the characteristic of the impedance signal over time; and determining a status of the catheter based on the comparison, the trend, or the rate of change.

36. The method of claim 31, further comprising:

determining a rate of change of the characteristic of the impedance signal over time; and controlling, by the processing circuitry, an operation of a peritoneal dialysis cycler based on the determined rate of change.

37. The method of claim 31, wherein the pressure signal is indicative of pressure external to the lumen and the impedance signal is indicative of impedance of fluid external to the lumen, the method further comprising:

at least one of comparing, by the processing circuitry, a characteristic of the pressure signal to a predetermined threshold pressure value or determining, by the processing circuitry, a first rate of change of the characteristic of the pressure signal over time;

at least one of comparing, by the processing circuitry, a characteristic of the impedance signal to a predetermined threshold impedance value or determining, by the processing circuitry, a second rate of change of the characteristic of the impedance signal over time; and controlling, by the processing circuitry, an operation of a peritoneal dialysis cycler based on at least one of the comparison of the characteristic of the pressure signal to the predetermined threshold pressure value or the first rate of change, and based on at least one of the comparison of the characteristic of the impedance signal to the predetermined threshold impedance value or the second rate of change.

\* \* \* \* \*